United States Patent
Kitano et al.

(10) Patent No.: US 6,734,205 B2
(45) Date of Patent: May 11, 2004

(54) SUBSTITUTED GUANIDINE DERIVATIVES

(75) Inventors: Masahumi Kitano, Takatsuki (JP); Masatoshi Yuri, Nishinomiya (JP); Naohito Ohashi, Takatsuki (JP)

(73) Assignee: Sumitomo Pharmaceuticals Company Limited, Osaka (JP)

( * ) Notice: Subject to any disclaimer, the term of this patent is extended or adjusted under 35 U.S.C. 154(b) by 0 days.

(21) Appl. No.: 10/168,112

(22) PCT Filed: Dec. 7, 2000

(86) PCT No.: PCT/JP00/08669
§ 371 (c)(1),
(2), (4) Date: Jun. 17, 2002

(87) PCT Pub. No.: WO01/44186
PCT Pub. Date: Jun. 21, 2001

(65) Prior Publication Data
US 2003/0018056 A1 Jan. 23, 2003

(30) Foreign Application Priority Data
Dec. 16, 1999 (JP) .......................... 11-356930
May 31, 2000 (JP) .......................... 2000-162669

(51) Int. Cl.[7] .................... A61K 31/404; C07F 9/38; C07D 209/42; A61P 9/06
(52) U.S. Cl. .................... 514/419; 548/414; 548/492
(58) Field of Search .................... 514/419; 548/414, 548/492

(56) References Cited

U.S. PATENT DOCUMENTS

| | | |
|---|---|---|
| 3,154,520 A | 10/1964 | Kitano et al. |
| 5,084,466 A | 1/1992 | Alig et al. |
| 5,814,654 A | 9/1998 | Kitano et al. |
| 5,834,454 A | 11/1998 | Kitano et al. |
| 5,852,046 A | 12/1998 | Lang et al. |
| 5,977,100 A | 11/1999 | Kitano et al. |
| 6,169,107 B1 | 1/2001 | Kitano et al. |
| 6,369,110 B1 | 4/2002 | Kitano et al. |

FOREIGN PATENT DOCUMENTS

| | | |
|---|---|---|
| EP | 126587 A1 | 11/1984 |
| EP | 0 126 587 A1 | 11/1984 |
| EP | 381033 A1 | 8/1990 |
| EP | 622356 A1 | 11/1994 |
| EP | 0 622 356 A1 | 11/1994 |
| EP | 0 639 573 A1 | 2/1995 |
| EP | 708091 A1 | 4/1996 |
| EP | 0 708 091 A1 | 4/1996 |
| EP | 0 803 501 A1 | 10/1997 |
| GB | 1 461 948 A | 1/1977 |
| GB | 1461948 | 1/1977 |
| JP | 10-237073 A | 9/1998 |
| JP | 10-310582 A | 11/1998 |
| WO | WO 94/26709 A1 | 11/1994 |
| WO | WO 97/36859 A1 | 10/1997 |
| WO | WO 99/55690 A1 | 11/1999 |
| WO | WO 00/44707 A1 | 8/2000 |

OTHER PUBLICATIONS

STN International ® CAPLUS Database, Accession No. 1996:379686; Kitano et al., abstract.*
M. Kitano et al., "Synthesis and Biological Activity of N–(Aminoiminomethyl)–1H–indole Carboxamide Derivatives as Na$^+$/H$^+$ Exchanger Inhibitors", *Chem. Pharm. Bull.*, vol. 47, No. 11, 1999, pp. 1538–1548.
C. Schmuck, "Side chain selective binding of N–acetyl–α–amino acid carboxylates by a 2–(guanidiniocarbonyl)pyrrole receptor in aqueous solvents", *Chem. Commun.*, (9), pp. 843–844 (1999).
Chemical Abstracts No. 179135v, *79–Inorganic Anal. Chem.*, vol. 108, 1988, p. 803.
S. Kamimura et al., "Metabolic Studies on N–Amidino–2–(2,6–dichlorophenyl) acetamide . . . Repeated Oral Administration", *Oyo Yakuri*, vol. 20, No. 5, 1980, pp. 745–751.
M. Kitano et al., "Synthesis and biological activity of N–(aminoiminomethyl)–1H–indole carboxamide derivatives as Na$^+$/H$^+$ exchanger inhibitors", *Chem. Pharm. Bull.*, vol. 47, No. 11, 1999, pp. 1538–1548.
C. Schmuck, "Side chain selective binding of N–acetyl–α–amino acid carboxylates by a 2–(guanidiniocarbonyl) pyrrole receptor in aqueous solvents," *Chem. Commun.*, vol. 9, 1999, pp. 843–844.
Chemical Abstracts, vol. 108, Abstract No. 179135 1988.
S. Kamimura et al., "Metabolic studies on N–amidino–2–(2, 6–dichlorophenyl)acetamide hydrochloride (guanfacine), a new antihypertensive agent. 2. Metabolites in blood, liver and excreta of rats after single and repeated oral adminstration", *Oyo Yakuri*, vol. 20, No. 5, 1980, pp. 745–751.

(List continued on next page.)

Primary Examiner—Robert W. Pamsuer
Assistant Examiner—Sonya Wright
(74) Attorney, Agent, or Firm—Sughrue Mion, PLLC

(57) ABSTRACT

A compound represented by the following formula:

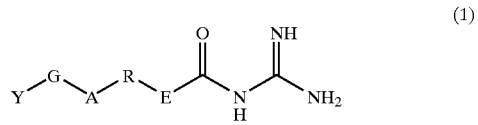

(1)

wherein R is a substituted or unsubstituted benzene ring, a fused polycyclic hydrocarbon ring which is substituted or unsubstituted, a monocyclic heterocyclic ring which is substituted or unsubstituted, a polycyclic heterocyclic ring which is substituted or unsubstituted, A and E are independently a single bond, a lower alkylene group or the like, G is a single bond, an oxygen atom or the like, and Y is a —SO$_3$H group or the like, a prodrug of said compound, or a pharmaceutically acceptable salt of said compound or prodrug is useful as a therapeutic or prophylactic agent for diseases caused by the acceleration of the sodium/proton exchange transport system.

10 Claims, No Drawings

OTHER PUBLICATIONS

Chemical Abstracts, vol. 95, No. 99321 1980.

R. Procaccine et al., "The subcellular distribution of 14C–lidamidine and its metabolites", *Drug Metab. Dispos.*, vol. 9, No. 3, 1981, pp. 202–206.

Chemical Abstracts, vol. 55, Column 3480, Para. F. to col. 3482, 1961.

*Chemical Abstracts*, vol. 55, 1961, column 3480, paragraph f to column 3482, paragraph a.

R.L. Procaccini et al., "The Subcellular Distribution of $^{14}$C–Lidamidine and Its Metabolites", *Drug Metabolism and Disposition*, vol. 9, No. 3, 1981, pp. 202–206.

Chemical Abstracts No. 99321b, "*40–Dyes*", vol. 95, 1981, p. 73 1980.

* cited by examiner

SUBSTITUTED GUANIDINE DERIVATIVES

This application is a 371 of PCT/JP00/08669 filed Dec. 7, 2000.

TECHNICAL FIELD

The present invention relates to novel substituted guanidine derivatives, prodrugs thereof or pharmaceutically acceptable salts of the derivatives or prodrugs, pharmaceutical uses of the derivatives, prodrugs or salts, and a process for production of the derivatives, prodrugs or salts. The compounds of the present invention inhibit the sodium/proton ($Na^+/H^+$) exchange transport system and hence are useful as a therapeutic or prophylactic agent for diseases caused by the acceleration of the sodium/proton ($Na^+/H^+$) exchange transport system, for example, hypertension, arrhythmia, angina pectoris, cardiac hypertrophy, cardiac insufficiency, diabetes mellitus, organ disorders associated with ischemia or ischemic reperfusion [e.g. cardiac ischemic reperfusion-injury, acute renal failure, or disorder induced by surgical treatment such as organ transplantation or percutaneous transluminal coronary angioplasty (PTCA)], diseases caused by hyperplasia such as hyperplasia of fibroblast, hyperplasia of smooth muscle cells or hyperplasia of mesangium cells, which diseases are, for example, atherosclerosis, pulmonary fibrosis, hepatic fibrosis, renal fibrosis, glomerular nephrosclerosis, organ hypertrophy, prostatic hypertrophy, diabetic complications or restenosis after PTCA, or diseases caused by endotherial cell injury.

BACKGROUND ART

As substituted guanidine derivatives having inhibitory effect on the sodium/proton ($Na^+/H^+$) exchange transport system, there may be exemplified the compounds disclosed in Japanese Patent Unexamined Publication Nos. 7-10839, 8-208602, 10-237073 and 9-291076 and International Publication No. WO 9961414.

In recent years, there has been reported the degeneration of nerve cells in mice which have underwent gene mutation relating to the sodium/proton ($Na^+/H^+$) exchange transport system (for instance, Cell, 91, 139–148 (1997)). It has been revealed that among known substituted guanidine derivatives having inhibitory effect on the sodium/proton ($Na^+/H^+$) exchange transport system, such as those exemplified above, there are substituted guanidine derivatives having an undesirable effect on nerve cells, i.e., substituted guanidine derivatives capable of degenerating nerve cells. It is suggested that such degeneration of nerve cells is likely to cause various neuropathies. Therefore, there is desired the development of a $Na^+/H^+$ exchange transport system inhibitor reduced in such an effect on nerve cells.

DISCLOSURE OF THE INVENTION

The present inventors earnestly investigated in order to achieve the above object, and consequently found that a compound represented by the general formula (1), a prodrug thereof or a pharmaceutically acceptable salt of the compound or prodrug (if necessary, the compound, prodrug or salt is hereinafter abbreviated as the present inventive compound in some cases) has an excellent inhibitory effect on the sodium/proton ($Na^+/H^+$) exchange transport system and exhibits only markedly lessened side effects on the nervous system, in particular, the central nervous system. That is, the present invention relates to the following.

[1]
A compound represented by the formula (1):

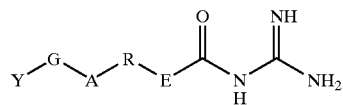

(1)

wherein R is a substituted or unsubstituted benzene ring, a fused polycyclic hydrocarbon ring which is substituted or unsubstituted, a monocyclic heterocyclic ring which is substituted or unsubstituted, or a polycyclic heterocyclic ring which is substituted or unsubstituted;

A and E are independently a single bond or a substituted or unsubstituted lower alkylene group (one or more of the —$CH_2$— groups of said lower alkylene group may be replaced by one or more groups, which may be the same or different and are selected from the groups consisting of a group represented by the formula: —O—, —S—, —N($R^1$)— or —C(=O)—, a benzene ring and a cycloalkane ring (one or more of the —$CH_2$— groups in said cycloalkane ring may be replaced by one or more groups, which may be the same or different and are represented by the formula: —O—, —S—, —N($R^2$)— or —C(=O)—) and any two adjacent atoms of said lower alkylene group may form a double bond or a triple bond);

G is a single bond or a group represented by the formula: —O— or —N($R^{11}$)—;

Y is a group represented by the formula: —$SO_3H$, —$PO_3H_2$, —$CO_2H$ or

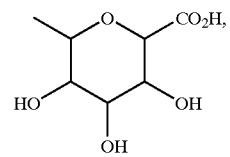

provided that G is a single bond when Y is a group represented by the formula: —$PO_3H_2$ or —$CO_2H$;

$R^1$, $R^{11}$ and $R^2$ are independently a hydrogen atom, a substituted or unsubstituted alkyl group, a substituted or unsubstituted alkenyl group, a substituted or unsubstituted alkynyl group, a substituted or unsubstituted cycloalkyl group, a substituted or unsubstituted cycloalkenyl group, a substituted or unsubstituted phenyl group, a substituted or unsubstituted naphthyl group, a substituted or unsubstituted heterocyclic group, a substituted or unsubstituted acyl group, or a group represented by the formula: —C(=O)N($R^5$)$R^6$,

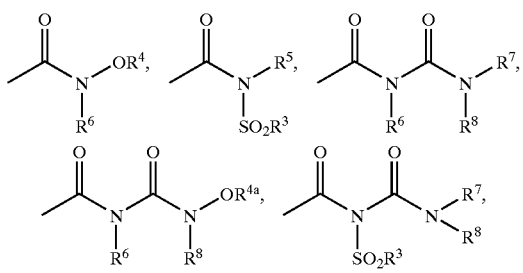

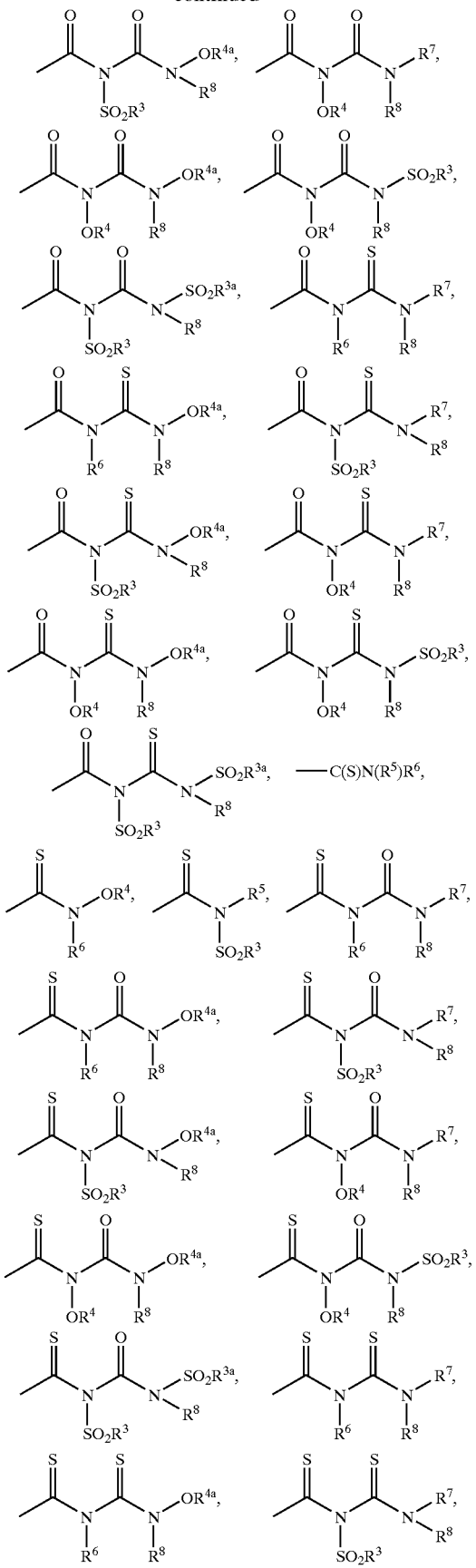
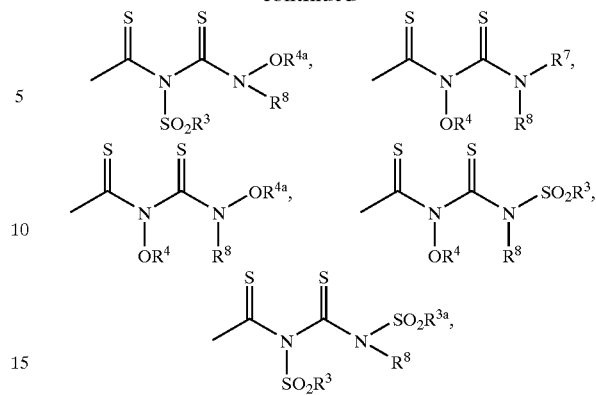

or —S(O)$_n$R$^3$.

R$^3$ and R$^{3a}$ are independently a hydroxyl group, a substituted or unsubstituted alkyl group, a substituted or unsubstituted phenyl group, a substituted or unsubstituted naphthyl group, or a substituted or unsubstituted heterocyclic group;

R$^5$, R$^6$, R$^7$ and R$^8$ are independently a hydrogen atom, a substituted or unsubstituted alkyl group, a substituted or unsubstituted alkenyl group, a substituted or unsubstituted alkynyl group, a substituted or unsubstituted cycloalkyl group, a substituted or unsubstituted cycloalkenyl group, a substituted or unsubstituted phenyl group, a substituted or unsubstituted naphthyl group, a substituted or unsubstituted heterocyclic group or a substituted or unsubstituted acyl group, or R$^5$ and R$^6$, or R$^7$ and R$^8$ may bind to each other to form, together with the nitrogen atom to which they are bonded, a 5- to 7-membered saturated cyclic amino group which may contain other heteroatom(s) in the ring and may be substituted by one or more substituted or unsubstituted alkyl groups, hydroxyl groups or —OR$^{4b}$ groups;

R$^4$, R$^{4a}$ and R$^{4b}$ are independently a hydrogen atom, a substituted or unsubstituted alkyl group, a substituted or unsubstituted cycloalkyl group, a substituted or unsubstituted cycloalkenyl group, a substituted or unsubstituted phenyl group, a substituted or unsubstituted naphthyl group, a substituted or unsubstituted heterocyclic group or —SO$_3$H; and n is an integer of 0, 1 or 2, or
a prodrug of said compound, or a pharmaceutically acceptable salt of said compound or prodrug.

[2]
A compound, a prodrug thereof or a pharmaceutically acceptable salt of the compound or prodrug according to the above item [1], wherein E is a single bond.

[3]
A compound, a prodrug thereof or a pharmaceutically acceptable salt of the compound or prodrug according to the above item [1] or [2], wherein A is a single bond, and G is a group represented by the formula: —O—.

[4]
A compound, a prodrug thereof or a pharmaceutically acceptable salt of the compound or prodrug according to the above item [1], [2] or [3], wherein Y is a group represented by the formula: —SO$_3$H.

[5]
A compound, a prodrug thereof or a pharmaceutically acceptable salt of the compound or prodrug according to the above item [1] or [2], wherein Y is a group represented by the formula: —PO$_3$H$_2$.

[6]
A compound, a prodrug thereof or a pharmaceutically acceptable salt of the compound or prodrug according to the above item [1], [4] or [5], wherein each of E and G is a single bond.

[7]
A compound, a prodrug thereof or a pharmaceutically acceptable salt of the compound or prodrug according to the above item [1] or [4], wherein each of E, A and G is a single bond.

[8]
A compound, a prodrug thereof or a pharmaceutically acceptable salt of the compound or prodrug according to the above item [2], [3], [4], [5], [6] or [7], wherein R is a substituted or unsubstituted indole.

[9]
A compound, a prodrug thereof or a pharmaceutically acceptable salt of the compound or prodrug according to the above item [2], [3], [4], [5], [6] or [7], wherein R is a substituted or unsubstituted benzene.

[10]
A compound, a prodrug thereof or a pharmaceutically acceptable salt of the compound or prodrug according to the above item [2], [3], [4], [5], [6] or [7], wherein R is 1H-indene, 1,2-dihydronaphthalene, 6,7-dihydro-5H-benzocycloheptene, 2,3-dihydro-1H-benz[b]azepine or 2,3-dihydro-benz[b]oxepine, which may be substituted or unsubstituted.

[11]
A compound, a prodrug thereof or a pharmaceutically acceptable salt of the compound or prodrug according to the above item [2], [3], [4], [5], [6] or [7], wherein R is a substituted or unsubstituted 6,7-dihydro-5H-benzocycloheptene.

[12]
A compound, a prodrug thereof or a pharmaceutically acceptable salt of the compound or prodrug according to the above item [2], [3], [4], [5], [6] or [7], wherein R is 1,3,4,5-tetrahydro-benz[cd]indole or 3,4,5,6-tetrahydro-1H-cyclohepta[cd]indole, which may be substituted or unsubstituted.

[13]
A compound, a prodrug thereof or a pharmaceutically acceptable salt of the compound or prodrug according to the above item [2], [3], [4], [5], [6] or [7], wherein R is 5,6-dihydro-4H-pyrrolo[3,2,1-ij]quinoline, 2,3-dihydro-pyrrolo[1,2,3-de][1,4]-benzoxazine, 2,3-dihydro-1H-pyrrolo[1,2,3-de]-quinoxaline, 4,5-dihydro-pyrrolo[3,2,1-hi]indole, 4,5,6,7-tetrahydro-pyrrolo[3,2,1-jk][1]benzazepine, 5,6,7,8-tetrahydro-4H-pyrrolo[3,2,1-kl][1]benzazocine, 4,5,7,8-tetrahydro-pyrrolo[3,2,1-kl]benz[e][1,4]-oxazocine or 4,5,7,8-tetrahydro-pyrrolo[3,2,1-kl]benzo[e][1,4]diazocine, which may be substituted or unsubstituted.

[14]
A compound, a prodrug thereof or a pharmaceutically acceptable salt of the compound or prodrug according to the above item [2], [3], [4], [5], [6] or [7], wherein R is 5,6,7,8-tetrahydro-4H-pyrrolo[3,2,1-kl][1]benzazocine, 4,5,7,8-tetrahydro-pyrrolo[3,2,1-kl]benz[e][1,4]oxazocine or 4,5,7,8-tetrahydro-pyrrolo[3,2,1-kl]benzo[e][1,4]diazocine, which may be substituted or unsubstituted.

[15]
A prodrug or pharmaceutically acceptable salt of a compound according to any one of the above items [1] to [14], wherein Y is a group represented by the formula: —SO$_3$R$^{40}$, —P(=O)(OH)(OR$^{41}$), —P(=O)(OR$^{42}$)(OR$^{43}$) or —C$_2$R$^{44}$ wherein R$^{40}$, R$^{41}$, R$^{42}$ R$^{43}$ and R$^{44}$ are independently a substituted or unsubstituted alkyl group.

[16]
A compound, a prodrug thereof or a pharmaceutically acceptable salt of the compound or prodrug according to the above item [1], which is selected from the group consisting of 2-[[[amino(imino)methyl]amino]carbonyl]-1-methyl-4-(trifluoromethyl)-1H-indol-6-yl hydrogen sulfate, 2-[[[amino(imino)methyl]amino]carbonyl]-1-methyl-4-(trifluoromethyl)-1H-indol-7-yl hydrogen sulfate, [2-[[[amino(imino)methyl]amino]carbonyl]-1-methyl-4-(trifluoromethyl)-1H-indol-6-yl]-methylphosphonic acid and 3-[2[[[amino(imino)methyl]amino]carbonyl]-4-chloro-1H-indol-1-yl]-1-propanesulfonic acid.

[17]
A pharmaceutical composition comprising a compound, a prodrug thereof or a pharmaceutically acceptable salt of the compound or prodrug according to any one of the above items [1] to [16].

[18]
A pharmaceutical composition for inhibiting the sodium/proton exchange transport system which comprises a compound, a prodrug thereof or a pharmaceutically acceptable salt of the compound or prodrug according to any one of the above items [1] to [16].

[19]
A pharmaceutical composition for the treatment or prophylaxis of hypertension, arrhythmia, angina pectoris, cardiac insufficiency, cardiac hypertrophy, diabetes mellitus, organ disorders associated with ischemia or ischemic reperfusion, diseases caused by excessive cell proliferation, or diseases caused by endothelial cell injury, which comprises a compound, a prodrug thereof or a pharmaceutically acceptable salt of the compound or prodrug according to any one of the above items [1] to [16].

[20]
A compound, a prodrug thereof or a pharmaceutically acceptable salt of the compound or prodrug according to any one of the above items [1] to [16], which is for use as an active ingredient of a pharmaceutical composition.

[21]
Use of a compound, a prodrug thereof or a pharmaceutically acceptable salt of the compound or prodrug according to any one of the above items [1] to [16] in the manufacture of a pharmaceutical composition for inhibiting the sodium/proton exchange transport system.

[22]
Use of a compound, a prodrug thereof or a pharmaceutically acceptable salt of the compound or prodrug according to any one of the above items [1] to [16] in the manufacture of a pharmaceutical composition for the treatment or prophylaxis of hypertension, arrhythmia, angina pectoris, cardiac insufficiency, cardiac hypertrophy, diabetes mellitus, organ disorders associated with ischemia or ischemic reperfusion, diseases caused by excessive cell proliferation, or diseases caused by endothelial cell injury.

[23]
A method for inhibiting the sodium/proton exchange transport system which comprises administering a compound, a prodrug thereof or a pharmaceutically acceptable salt of the compound or prodrug according to any one of the above items [1] to [16] to an object for the administration, in an effective amount.

[24]
A method for treating or preventing hypertension, arrhythmia, angina pectoris, cardiac insufficiency, cardiac hypertrophy, diabetes mellitus, organ disorders associated with ischemia or ischemic reperfusion, diseases caused by excessive cell proliferation, or diseases caused by endothelial cell injury, which comprises administering a compound, a prodrug thereof or a pharmaceutically acceptable salt of the compound or prodrug according to any one of the above items [1] to [16] to an object for the administration, in an effective amount.

[25]

A process for producing a compound represented by the formula (1):

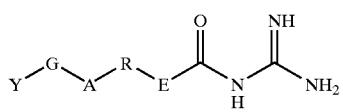

(1)

wherein Y, G, A, R and E are as defined in the above item [1], a prodrug thereof or a pharmaceutically acceptable salt of the compound or prodrug, which comprises reacting a compound represented by the formula (2):

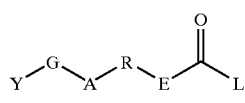

(2)

wherein Y, G, A, R and E are as defined in the above item [1], and L is a hydroxyl group or a leaving group which may be substituted by a nucleophilic reagent, with guanidine.

A prodrug or pharmaceutically acceptable salt of a compound represented by the formula (1):

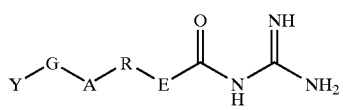

(1)

wherein E is a single bond; wherein R is a substituted or unsubstituted indole; wherein the group represented by —C(O)NHC(NH)NH$_2$ in the formula (1) is attached to 2-position thereof;

A is a single bond or a substituted or unsubstituted lower alkylene group (one or more of the —CH$_2$— groups of said lower alkylene group may be replaced by one or more groups, which may be the same or different and are selected from the group consisting of a group represented by the formula: —O—, —S—, —N(R$^1$)— or —C(=O)—, a benzene ring and a cycloalkane ring (one or more of the —CH$_2$— groups in said cycloalkane ring may be replaced by one or more groups, which may be the same or different and are represented by the formula: —O—, —S—, —N(R$^2$)— or —C(=O)—) and any two adjacent atoms of said lower alkylene group may form a double bond or a triple bond);

G is a single bond or a group represented by the formula: —O— or —N(R$^{11}$)—;

R$^1$, R$^{11}$ and R$^2$ are independently a hydrogen atom, a substituted or unsubstituted alkyl group, a substituted or unsubstituted alkenyl group, a substituted or unsubstituted alkynyl group, a substituted or unsubstituted cycloalkyl group, a substituted or unsubstituted cycloalkenyl group, a substituted or unsubstituted phenyl group, a substituted or unsubstituted naphthyl group, a substituted or unsubstituted heterocyclic group, a substituted or unsubstituted acyl group; or a prodrug of said compound, or a pharmaceutically acceptable salt of said compound or prodrug;

Y is a group represented by the formula: —SO$_3$R$^{40}$, —P(=O)(OH)(OR$^{41}$), or —P(=O)(OR$^{42}$)(OR$^{43}$) wherein R$^{40}$, R$^{41}$, R$^{42}$, and R$^{43}$ are independently a substituted or unsubstituted alkyl group.

[26]

A process for producing a compound which may be replaced by the formula (12):

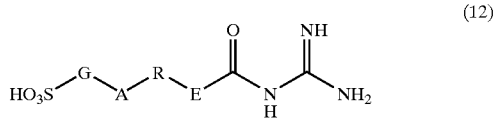

(12)

wherein G, A, R and E are as defined above, a prodrug thereof or a pharmaceutically acceptable salt of the compound or prodrug, which comprises reacting a compound represented by the formula (3):

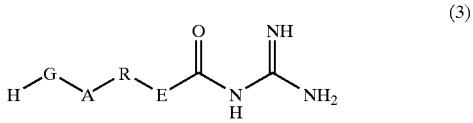

(3)

wherein A, R and E are as defined in the above item [1], and G is a group represented by the formula —O— or —N(R$^{11}$)— wherein R$^{11}$ is as defined in the above item [1], with sulfur trioxide (SO$_3$) or a complex thereof.

BEST MODE FOR CARRYING OUT THE INVENTION

Compounds having inhibitory effect on the Na$^+$/H$^+$ exchange transport system exhibit a variety of pharmacokinetics, depending on their structures. For reducing side effects and the like, drugs capable of being distributed in desirable sites of action but not in undesirable sites are preferable. The compound of the present invention has a property of being hardly distributed in, in particular, the central nervous system in the case of its general administration such as oral administration or intravenous administration. Therefore, it is conjectured that the compound of the present invention has little side effect on central nervous system when used as a therapeutic or prophylactic agent for hypertension, arrhythmia, angina pectoris, cardiac insufficiency, cardiac hypertrophy, diabetes mellitus, organ disorders associated with ischemia or ischemic reperfusion [e.g. cardiac ischemic reperfusion-injury, acute renal failure, or disorder induced by surgical treatment such as organ transplantation or percutaneous transluminal coronary angioplasty (PTCA)], diseases caused by hyperplasia such as hyperplasia of fibroblast, hyperplasia of smooth muscle cells or hyperplasia of mesangium cells, which diseases are, for example, atherosclerosis, pulmonary fibrosis, hepatic fibrosis, renal fibrosis, glomerular nephrosclerosis, organ hypertrophy, prostatic hypertrophy, diabetic complications or restenosis after PTCA, or diseases caused by endotherial cell injury.

The various groups in the present invention are explained below. Unless otherwise specified, the following explanation applies to the case where each of the groups is a portion of another group.

The terms "fused polycyclic hydrocarbon ring", "monocyclic heterocyclic ring" and "polycyclic heterocyclic ring" for R mean rings, respectively, formed by the conversion of two of the hydrogen atoms of the corresponding ring explained below to bonds. The specific names of the rings for R are described in the above items [6] to [12]. They also mean rings, respectively, formed by the conversion of two of the hydrogen atoms of a corresponding ring to bonds.

The heterocyclic group includes monocyclic heterocyclic groups and polycyclic heterocyclic groups. The terms "monocyclic heterocyclic group" and "polycyclic heterocyclic group" mean groups formed by the conversion of one of the hydrogen atoms of the monocyclic heterocyclic ring or polycyclic heterocyclic ring, respectively, explained below to a bond.

The term "fused polycyclic hydrocarbon ring group" means a group formed by the conversion of one of the hydrogen atoms of the fused polycyclic hydrocarbon ring explained below to a bond.

The term "saturated heterocyclic group" means a group formed by the conversion of one of the hydrogen atoms of the saturated heterocyclic ring explained below to a bond.

The saturated heterocyclic ring includes the undermentioned 3- to 8-membered, saturated, heterocyclic and monocyclic rings containing 1 to 4 nitrogen atoms, 3- to 8-membered, saturated, heterocyclic and monocyclic rings containing 1 to 3 nitrogen atoms and one or two oxygen atoms, and 3- to 8-membered, saturated, heterocyclic and monocyclic rings containing 1 to 3 nitrogen atoms and one or two sulfur atoms.

The fused polycyclic hydrocarbon ring includes, for example, fused polycyclic hydrocarbon ring groups of 16 or less carbon atoms, such as indene, naphthalene, azulene, fluorene, phenalene, phenanthrene, anthracene, acephenanthrylene, 1,2-dihydronaphthalene, 6,7-dihydro-5H-benzocycloheptene, benzocyclooctene, etc. Preferable examples of the fused polycyclic hydrocarbon ring are indene, naphthalene and 6,7-dihydro-5H-benzocycloheptene.

The monocyclic heterocyclic ring includes 3- to 8-membered, unsaturated, heterocyclic and monocyclic rings containing 1 to 4 nitrogen atoms, 3- to 8-membered, saturated, heterocyclic and monocyclic rings containing 1 to 4 nitrogen atoms, 3- to 8-membered, unsaturated, heterocyclic and monocyclic rings containing an oxygen atom, 3- to 8-membered, unsaturated, heterocyclic and monocyclic rings containing one or two sulfur atoms, 3- to 8-membered, unsaturated, heterocyclic and monocyclic rings containing 1 to 3 nitrogen atoms and one or two oxygen atoms, 3- to 8-membered, saturated, heterocyclic and monocyclic rings containing 1 to 3 nitrogen atoms and one or two oxygen atoms, 3- to 8-membered, unsaturated, heterocyclic and monocyclic rings containing 1 to 3 nitrogen atoms and one or two sulfur atoms, 3- to 8-membered, saturated, heterocyclic and monocyclic rings containing 1 to 3 nitrogen atoms and one or two sulfur atoms, and 3- to 8-membered, unsaturated, heterocyclic and monocyclic rings containing an oxygen atom and one or two sulfur atoms.

The 3- to 8-membered, unsaturated, heterocyclic and monocyclic rings containing 1 to 4 nitrogen atoms include, for example, pyrrole, pyrroline, pyridine, dihydropyridine, imidazole, pyrazole, imidazoline, pyrazine, pyrimidine, pyridazine, pyrazole, triazole and tetrazole. Preferable examples thereof are pyrrole, pyridine, imidazole, pyrazine, pyrimidine, etc.

The 3- to 8-membered, saturated, heterocyclic and monocyclic rings containing 1 to 4 nitrogen atoms include, for example, pyrrolidine, piperidine, imidazolidine, pyrazolidine and piperazine.

The 3- to 8-membered, unsaturated, heterocyclic and monocyclic rings containing an oxygen atom include, for example, furan and pyran.

The 3- to 8-membered, unsaturated, heterocyclic and monocyclic rings containing one or two sulfur atoms include, for example, thiophene, dihydrodithiin and dihydrodithion.

The 3- to 8-membered, unsaturated, heterocyclic and monocyclic rings containing 1 to 3 nitrogen atoms and one or two oxygen atoms include, for example, oxazole, oxadiazole and isoxazole.

The 3- to 8-membered, saturated, heterocyclic and monocyclic rings containing 1 to 3 nitrogen atoms and one or two oxygen atoms include, for example, morpholine and oxazolidine.

The 3- to 8-membered, unsaturated, heterocyclic and monocyclic rings containing 1 to 3 nitrogen atoms and one or two sulfur atoms include, for example, thiazole, isothiazole and thiadiazole.

The 3- to 8-membered, saturated, heterocyclic and monocyclic rings containing 1 to 3 nitrogen atoms and one or two sulfur atoms include, for example, thiazolidine.

The 3- to 8-membered, unsaturated, heterocyclic and monocyclic rings containing an oxygen atom and one or two sulfur atoms include, for example, dihydrooxathiin.

The polycyclic heterocyclic ring includes, for example, unsaturated fused heterocyclic rings containing 1 to 4 nitrogen atoms, unsaturated fused heterocyclic rings containing 1 to 3 nitrogen atoms and one or two oxygen atoms, unsaturated fused heterocyclic rings containing 1 to 3 nitrogen atoms and one or two sulfur atoms, unsaturated fused heterocyclic rings containing one or two oxygen atoms, unsaturated fused heterocyclic rings containing an oxygen atom and one or two sulfur atoms, and unsaturated fused heterocyclic rings containing one or two sulfur atoms.

The unsaturated fused heterocyclic rings containing 1 to 4 nitrogen atoms include, for example, indole, isoindole, indoline, quinoline, isoquinoline, quinolizine, indazole, phthalazine, naphthyridine, quinoxaline, quinazoline, cinnoline, carbazole, purine, pteridine, phenazine, carboline, phenanthridine, acridine, indoline, isoindoline, 1,2-dihydroisoquinoline, benzimidazole, imidazopyridine, benzotriazole, tetrahydroimidazopyridine, benz[b]azepine, benz[cd]indole, cyclohepta[cd]indole, pyrrolo[3,2,1-ij]quinoline, cyclohexa[b]pyridine, cyclohepta[b]pyridine, pyrrolo[1,2,3-de]quinoxaline, pyrrolo[3,2,1-hi]indole, pyrrolo[3,2,1-jk][1]-benzazepine, pyrrolo[3,2,1-kl][1]benzazocine and pyrrolo[3,2,1-kl]benzo-[e][1,4]diazocine. Preferable examples thereof are indole, quinoline, isoquinoline, phthalazine, naphthyridine, quinoxaline, quinazoline, cinnoline, carbazole, indoline, benzimidazole, 1,2-dihydroisoquinoline, benz[b]azepine, benz[cd]indole, cyclohepta[cd]indole, cyclohexa[b]pyridine, cyclohepta[b]pyridine, pyrrolo[3,2,1-ij]quinoline, pyrrolo[1,2,3-de]quinoxaline, pyrrolo[3,2,1-hi]indole, pyrrolo[3,2,1-jk][1]benzazepine, pyrrolo[3,2,1-kl][1]-benzazocine, and pyrrolo [3,2,1-kl]benzo[e][1,4]-diazocine. More preferable examples thereof are indole, 1,2-dihydroisoquinoline, benz[b]azepine, benz[cd]indole, cyclohepta[cd]indole, cyclohexa[b]pyridine, cyclohepta[b]pyridine, pyrrolo[3,2,1-jk][1]benzazepine, pyrrolo[3,2,1-kl][1]benzazocine, and pyrrolo[3,2,1-kl]benzo[e][1,4]diazocine.

The unsaturated fused heterocyclic rings containing 1 to 3 nitrogen atoms and one or two oxygen atoms include, for example, benzoxazole, benzoxadiazole, phenoxazine, pyrrolo[1,2,3-de][1,4]benzoxazine, pyrrolo[2,1-c][1,4]benzoxazine, and pyrrolo[3,2,1-kl]benz[e][4,1]oxazocine. Preferable examples thereof are benzoxazole, pyrrolo[1,2,3-de][1,4]benzoxazine, pyrrolo[2,1-c][1,4]benzoxazine and pyrrolo[3,2,1-kl]benz[e][4,1]oxazocine.

The unsaturated fused heterocyclic rings containing 1 to 3 nitrogen atoms and one or two sulfur atoms include, for example, benzothiazole, benzothiadiazole, 1,4-benzothiazine and phenothiazine. Preferable examples thereof are benzothiazole and 1,4-benzothiazine.

The unsaturated fused heterocyclic rings containing one or two oxygen atoms include, for example, benzofuran, dihydrobenzofuran, chromene, isobenzofuran, xanthene, isochroman, chroman and benz[b]oxepine. Preferable examples thereof are benzofuran, benz[b]oxepine, etc.

The unsaturated fused heterocyclic rings containing an oxygen atom and one or two sulfur atoms include, for example, 1,4-benzoxathiin, phenoxathiin, etc.

The unsaturated fused heterocyclic rings containing one or two sulfur atoms include, for example, benzothiophene, benzothiin, benzothiopyran, thiochroman and thianthrene. Preferable examples thereof are benzothiophene, benzothiopyran and thiochroman.

Each of the benzene ring, fused polycyclic hydrocarbon ring, monocyclic heterocyclic ring and polycyclic heterocyclic ring may have one or more substituents which may be the same or different. The substituents include, for example, hydrogen atom, substituted or unsubstituted alkyl groups, substituted or unsubstituted alkenyl groups, substituted or unsubstituted alkynyl groups, substituted or unsubstituted cycloalkyl groups, substituted or unsubstituted cycloalkenyl groups, substituted or unsubstituted phenyl groups, substituted or unsubstituted naphthyl groups, substituted or unsubstituted heterocyclic groups, substituted or unsubstituted acyl groups, carboxyl group, halogen atoms, nitro group and groups represented by the formulas —CN, —OR$^{14}$, —N(R$^{15}$)R$^{16}$,

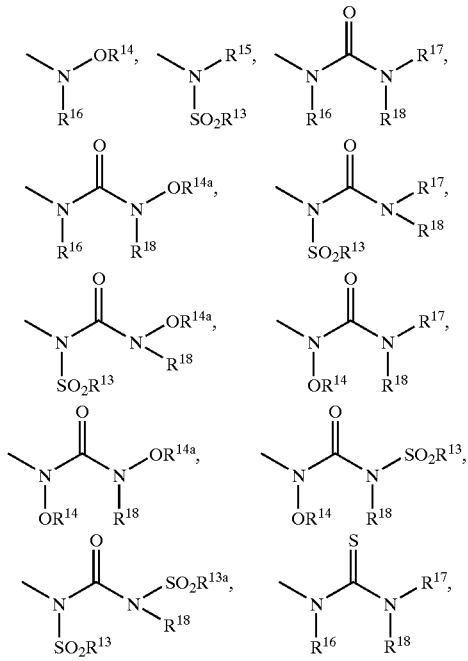

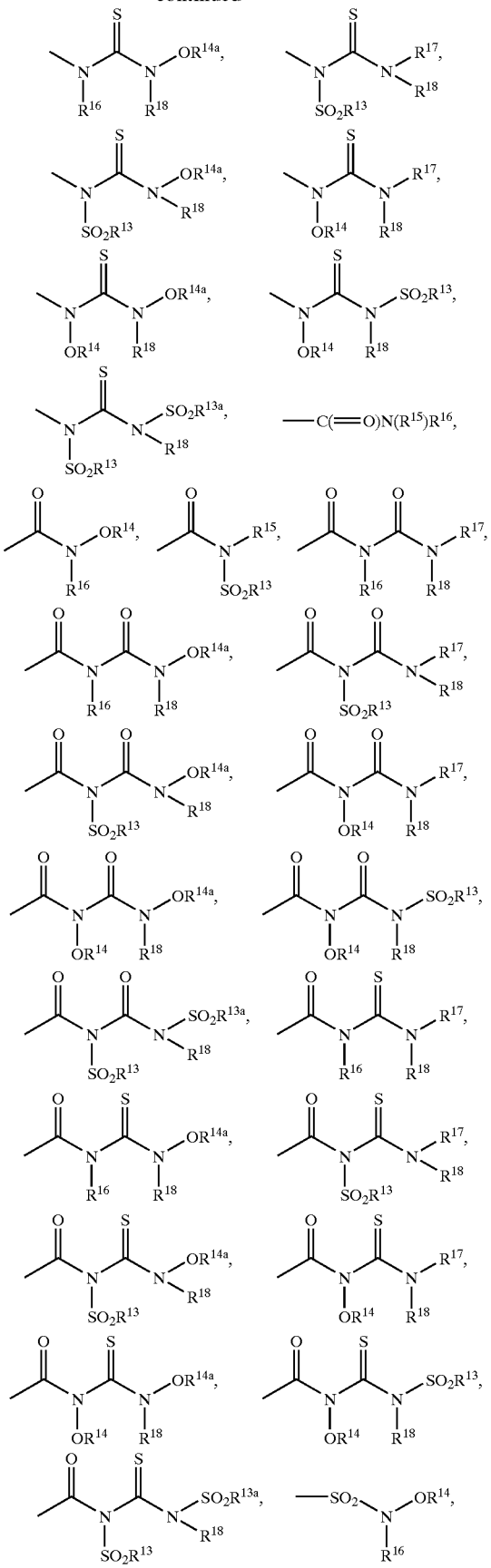

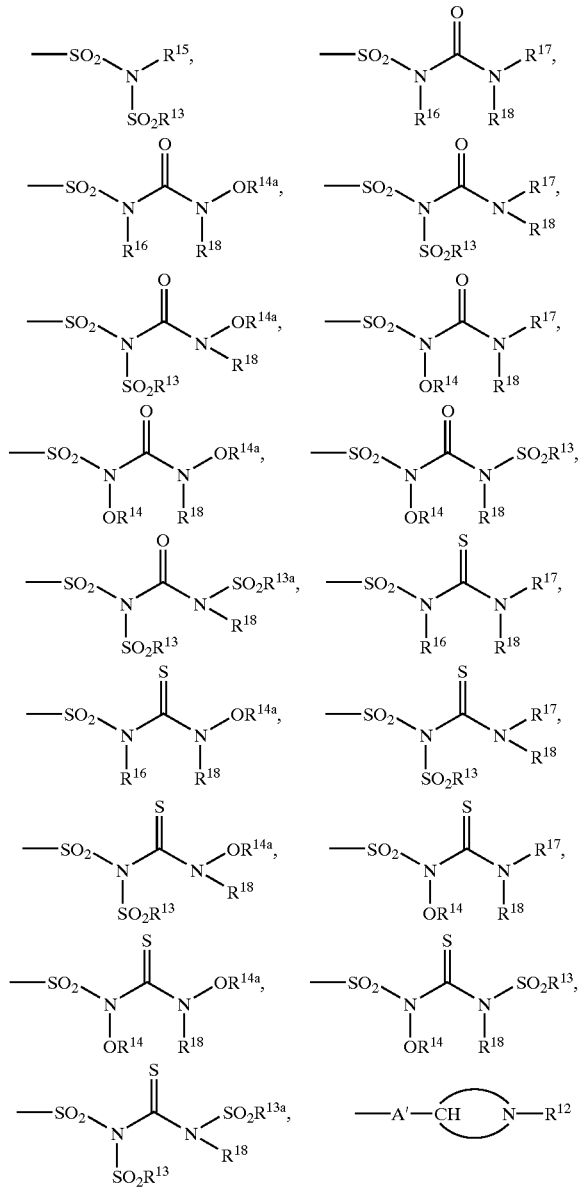

(wherein A' is an oxygen atom, —S(O)$_n$— or —N(R$^{21}$)—, m is an integer of 0, 1 or 2, R$^{12}$ and R$^{21}$ are independently a hydrogen atom, an alkyl group, an alkenyl group, an alkynyl group, a cycloalkyl group, a phenyl group, a naphthyl group, a heterocyclic group or an acyl group, and the ring is a 3- to 8-membered saturated heterocyclic group comprising a nitrogen atom and carbon atoms), and —S(O)$_n$R$^{13}$.

R$^{13}$ and R$^{13a}$ are independently a hydroxyl group, a substituted or unsubstituted alkyl group, a substituted or unsubstituted phenyl group, a substituted or unsubstituted naphthyl group or a substituted or unsubstituted heterocyclic group.

R$^{15}$, R$^6$, R$^{17}$ and R$^{18}$ are independently a hydrogen atom, a substituted or unsubstituted alkyl group, a substituted or unsubstituted alkenyl group, a substituted or unsubstituted alkynyl group, a substituted or unsubstituted cycloalkyl group, a substituted or unsubstituted cycloalkenyl group, a substituted or unsubstituted phenyl group, a substituted or unsubstituted naphthyl group, a substituted or unsubstituted heterocyclic group, or a substituted or unsubstituted acyl group, or R$^{15}$ and R$^{16}$, or R$^{17}$ and R$^{18}$ may bind to each other to form, together with the nitrogen atom to which they are bonded, a 5- to 7-membered saturated cyclic amino group which may contain other heteroatom(s) in the ring and may be substituted by one or more substituted or unsubstituted alkyl groups, hydroxyl groups or —OR$^{14b}$ groups.

R$^{14}$, R$^{14a}$ and R$^{14b}$ are independently a hydrogen atom, an alkyl group, a cycloalkyl group, a cycloalkenyl group, a phenyl group, a naphthyl group, a heterocyclic group or —SO$_3$H.

For each of R$^{15}$, R$^{16}$, R$^{17}$ and R$^{18}$, the substituted alkyl group has one or more substituents which may be the same or different. The substituted alkyl group includes, for example, alkyl groups of 1 to 5 carbon atoms substituted by a cycloalkyl group of 3 to 6 carbon atoms, polyhaloalkyl groups of 1 to 5 carbon atoms, hydroxyalkyl groups of 1 to 6 carbon atoms, alkoxyalkyl groups of 2 to 6 carbon atoms, cyanoalkyl groups of 2 to 6 carbon atoms, carboxyalkyl groups of 2 to 6 carbon atoms, alkoxycarbonylalkyl groups of 3 to 8 carbon atoms, alkanoylalkyl groups of 3 to 8 carbon atoms, aroylalkyl groups of 16 or less carbon atoms, phenyl- or naphthyl-C1~C5 alkyl groups, carbamoyl-C1~C3 alkyl groups which may have one or two C1~C3 alkyl groups as a substituent(s) on the nitrogen atom, amino-C1~C5 alkyl groups which may have one or two C1~C3 alkyl or C7~C11 aralkyl groups as a substituent(s) on the nitrogen atom, and 5- to 7-membered saturated cyclic amino-C1~C3 alkyl groups.

In the present specification, unless otherwise specified, each of phenyl group, naphthyl group, a fused polycyclic hydrocarbon group, heterocyclic groups (a monocyclic heterocyclic group and a polycyclic heterocyclic group), an aroyl group, a saturated heterocyclic ring-carbonyl group and a heterocyclic aromatic acyl group may have one or more substituents which may be the same or different. The substituents include, for example, alkyl groups, alkenyl groups, alkynyl groups, cycloalkyl groups, cycloalkenyl groups, saturated heterocyclic groups, phenyl group, naphthyl group, heterocyclic groups, acyl groups, carboxyl group, halogen atoms and nitro group, etc.

Each of the cycloalkyl groups, cycloalkenyl groups and cycloalkanecarbonyl groups may have 1 to 4 substituents which may be the same or different. The substituents include, for example, alkyl groups, substituted alkyl groups, hydroxyl group, and groups represented by the formula —OR$^{34}$.

As the group represented by R$^{34}$, there may be exemplified the same groups as those exemplified as the group represented by R$^4$.

As the alkyl groups, there may be exemplified linear or branched alkyl groups of 8 or less carbon atoms, such as methyl, ethyl, propyl, 2-propyl, butyl, 2-butyl, 2-methylpropyl, 1,1-dimethylethyl, pentyl, hexyl, heptyl, octyl, etc.

As the cycloalkyl groups, there may be exemplified 3- to 8-membered cycloalkyl groups such as cyclopropyl, cyclobutyl, cyclopentyl, cyclohexyl, cycloheptyl, 2-methylcyclopentyl, 3-methylcyclopentyl, 2-methylcyclohexyl, 3-methylcyclohexyl, 4-methylcyclohexyl, 2-hydroxycyclopentyl, 3-hydroxycyclopentyl, 2-hydroxycyclohexyl, 3-hydroxycyclohexyl, 4-hydroxycyclohexyl, 2-(hydroxymethyl)cyclopentyl, 3-(hydroxymethyl)cyclopentyl, 2-(hydroxymethyl)cyclohexyl, 3-(hydroxymethyl)cyclohexyl, 4-(hydroxymethyl)cyclohexyl, 2-(aminomethyl)cyclopentyl, 3-(aminomethyl)cyclopentyl, 2-(aminomethyl)cyclohexyl, 3-(aminomethyl)cyclohexyl, 4-(aminomethyl)cyclohexyl, 2-(methoxymethyl)cyclopentyl, 3-(methoxymethyl)cyclopentyl, 2-(methoxymethyl)cyclohexyl, 3-(methoxymethyl)cyclohexyl, 4-(methoxymethyl)cyclohexyl, etc.

The term "cycloalkane ring" in the definition of A and E means a divalent group formed by the conversion of two of the hydrogen atoms of a cycloalkane ring to direct links. Specific examples thereof are 3- to 8-membered cycloalkane rings. More specific examples thereof are divalent groups formed by the conversion of one of the hydrogen atoms of the above-exemplified cycloalkyl group to a direct link.

As the cycloalkenyl groups, there may be exemplified 3- to 8-membered cycloalkenyl groups having a double bond, such as 1-cyclopentenyl, 2-cyclopentenyl, 3-cyclopentenyl, 1-cyclohexenyl, 2-cyclohexenyl, 3-cyclohexenyl, etc.

As the alkenyl groups, there may be exemplified those having 6 or less carbon atoms, such as vinyl, allyl, propenyl, 2-propenyl, butenyl, pentenyl, hexenyl, etc.

As the alkynyl groups, there may be exemplified those having 6 or less carbon atoms, such as ethynyl, propargyl, butynyl, pentynyl, etc.

The halogen atoms include, for example, iodine, fluorine, chlorine and bromine atoms.

The acyl groups include, for example, formyl group; alkanoyl groups of 2 to 6 carbon atoms, such as acetyl, propanoyl, etc.; cycloalkanecarbonyl groups of 4 to 7 carbon atoms, such as cyclopropanecarbonyl, cyclobutanecarbonyl, cyclopentanecarbonyl, cyclohexanecarbonyl, etc.; cycloalkenecarbonyl groups of 3 to 6 carbon atoms, such as. cyclopentenecarbonyl, cyclohexenecarbonyl, etc.; aroyl groups of 6 to 10 carbon atoms, such as benzoyl, toluoyl, naphthoyl, etc.; saturated heterocyclic ring-carbonyl groups having a 5- or 6-membered saturated heterocyclic ring containing one or two heteroatoms selected from nitrogen atom, oxygen atom and sulfur atom, for example, 2-piperidinecarbonyl, 3-morpholinecarbonyl, etc.; and heteroaromatic acyl groups having a 5- or 6-membered heteroaromatic ring containing one or two heteroatoms selected from nitrogen atom, oxygen atom and sulfur atom, for example, furoyl, thenoyl, nicotinoyl, isonicotinoyl, etc.

The substituted alkyl group may have one or more substituents which may be the same or different. The substituents include halogen atoms, hydroxyl group, alkoxy groups, cycloalkyl groups, cyano group, carboxyl group, acyl groups, substituted or unsubstituted phenyl groups, substituted or unsubstituted naphthyl groups, substituted or unsubstituted heterocyclic groups, oxo group, thioxo group, and groups represented by the formula —CONRpRq (wherein Rp and Rq are independently a hydrogen atom or an alkyl group, or Rp and Rq bind to each other to form a 5- to 7-membered cyclic amino group which may contain other heteroatom(s) in the ring), —SO$_2$R$^{33}$, —SO$_2$N(R$^{35}$)R$^{36}$, —N(R$^{35}$) R$^{36}$ or

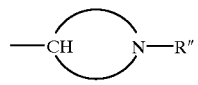

wherein R" is a hydrogen atom, an alkyl group or a substituted alkyl group, the ring is a 3- to 8-membered saturated heterocyclic group comprising a nitrogen atom and carbon atoms, and the substituent of the substituted alkyl group includes halogen atoms, hydroxyl group, alkoxy groups, cycloalkyl groups, cyano group, carboxyl group, acyl groups, phenyl group, naphthyl group, heterocyclic groups, oxo group and thioxo group.

As R$^{33}$, R$^{35}$ and R$^{36}$, there may be exemplified the same groups as those exemplified above as R$^{13}$, R$^{15}$ and R$^{16}$, respectively.

Such a substituted alkyl group includes, for example, alkyl groups of 1 to 5 carbon atoms substituted by a cycloalkyl group of 3 to 6 carbon atoms; polyhaloalkyl groups of 1 to 5 carbon atoms; hydroxyalkyl groups of 1 to 6 carbon atoms; alkoxyalkyl groups of 2 to 6 carbon atoms; cyanoalkyl groups of 2 to 6 carbon atoms; carboxyalkyl groups of 2 to 6 carbon atoms; alkoxycarbonylalkyl groups of 3 to 8 carbon atoms; alkanoylalkyl groups of 3 to 8 carbon atoms; aroylalkyl groups of 16 or less carbon atoms; substituted or unsubstituted phenyl- or naphthyl-C1~C5 alkyl groups; carbamoyl-C1~C3 alkyl groups which may have one or two C1~C3 alkyl groups as a substituent(s) on the nitrogen atom; amino-C1~C5 alkyl groups which may have one or two C1~C3 alkyl or C7~C11 aralkyl groups as a substituent(s) on the nitrogen atom; and 5- to 7-membered saturated cyclic amino-C1~C3 alkyl groups.

Typical examples of the substituted alkyl group are polyhaloalkyl groups of 1 to 3 carbon atoms, such as trifluoromethyl, trifluoroethyl, trichloromethyl, etc.; hydroxyalkyl groups of 1 to 6 carbon atoms, such as hydroxymethyl, hydroxyethyl, 1-hydroxyethyl, etc.; aminoalkyl groups of 1 to 5 carbon atoms, such as aminomethyl, aminoethyl, 1-aminoethyl, etc.; alkoxyalkyl groups of 1 to 6 carbon atoms, such as methoxyethyl, ethoxyethyl, methoxypropyl, etc.; carboxyalkyl groups of 2 to 6 carbon atoms, such as carboxyethyl, carboxypropyl, etc.; alkoxycarbonylalkyl groups of 3 to 7 carbon atoms, such as methoxycarbonylmethyl, ethoxycarbonylmethyl, methoxycarbonylethyl, etc.; phenyl- or naphthyl-C1~C5 alkyl group (which may have in the phenyl or naphthyl portion a substituent such as a C1~C3 alkyl group, halogen atom, nitro group, amino group, hydroxyl group, C1~C3 alkoxy group or the like) such as benzyl, phenylethyl, phenylpropyl, phenylbutyl, 1- or 2-naphthylmethyl, etc.; carbamoyl-C1~C3 alkyl groups which may have one or two C$_1$~C$_3$ alkyl groups as a substituent(s) on the nitrogen atom, for example, carbamoylmethyl, carbamoylethyl, dimethylcarbamoylmethyl, etc.; amino-C1~C5 alkyl groups which may have one or two C1~C3 alkyl or C7~C11 aralkyl groups as a substituent(s) on the nitrogen atom, for example, aminoethyl, aminopropyl, dimethylaminoethyl, dimethylaminopropyl, dimethylaminoethyl, N-methyl-N-benzylaminoethyl, etc.; and 5- to 7-membered saturated cyclic amino-C1~C3 alkyl groups such as 1-pyrrolidinylethyl, piperidinoethyl, etc. For R$^5$, R$^6$, R$^{15}$, R$^{16}$, R$^7$, R$^8$, R$^{17}$ and R$^{18}$, phenyl-C1~C5 alkyl groups such as phenylethyl and the like may be exemplified as the substituted alkyl group.

As the substituent of each of the substituted alkenyl group, the substituted alkynyl group and the substituted alkanoyl group, there may be exemplified the same groups as those exemplified above as the substituent of the substituted alkyl group. These substituted groups also may have one or more substituents which may be the same or different.

As the aralkyl group, alkyl groups substituted by a phenyl group or a fused polycyclic hydrocarbon ring group may be exemplified.

Oxygen atom, nitrogen atom and sulfur atom may be exemplified as the heteroatom(s) of the 5- to 7-membered saturated cyclic amino group which R$^5$ and R$^6$; R$^{15}$ and R$^{16}$; R$^7$ and R$^8$; R$^{17}$ and R$^{18}$; or Rp and Rq form together with the nitrogen atom to which they are bonded, by binding to each other and which may contain other heteroatom(s) in the ring. Specific examples of the 5- to 7-membered saturated cyclic amino group are 5- to 7-membered ring groups containing 1 to 3 nitrogen atoms and 5- to 7-membered ring groups containing a nitrogen atom and an oxygen atom. More specific examples thereof are 1-pyrrolidinyl, 1-piperidino, 1-piperazinyl, morpholino, 1-(4-methyl) piperazinyl, etc.

As the group represented by the formula —S(O)$_2$R$^3$, —S(O)$_2$R$^{3a}$, —S(O)$_2$R$^{13}$ or —S(O)$_2$R$^{13a}$, there may be exemplified alkylsulfonyl groups of 8 or less carbon atoms, such as methylsulfonyl group, ethylsulfonyl group, propylsulfonyl group, isopropylsulfonyl group, etc. As the group represented by the formula —S(O)$_n$R$^3$, there may be exemplified the above-exemplified groups, corresponding alkylsulfinyl or alkylthio groups, and sulfo group.

Each of the lower alkylene group, the alkenylene group and the alkynylene group may have one or more substituents which may be the same or different. The substituents include, for example, halogen atoms, alkyl groups, substituted alkyl groups, cycloalkyl groups, cycloalkenyl groups, saturated heterocyclic groups, carboxyl group, alkoxycarbonyl groups, phenyl group, naphthyl group, heterocyclic groups, and groups represented by the formula —CON(R$^{45}$)R$^{46}$.

As R$^{45}$ and R$^{46}$, there may be exemplified the same groups as those exemplified above as R$^{15}$ and R$^{16}$.

As the lower alkylene group, there may be exemplified alkylene groups of 10 or less carbon atoms, such as methylene, ethylene, trimethylene, tetramethylene, pentamethylene, hexamethylene, etc.

As the group represented by the formula:

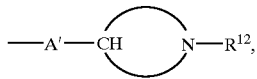

there may be exemplified groups represented by the following formulas:

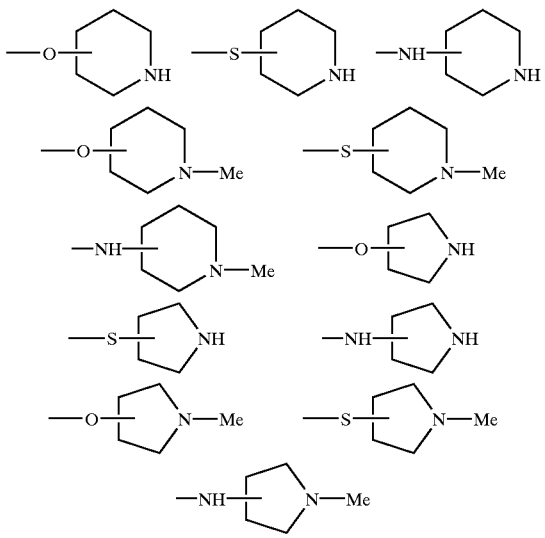

Preferable examples thereof are (piperidin-3-yl)oxy, (piperidin-4-yl)oxy, (1-methylpiperidin-3-yl)oxy, (1-methylpiperidin-4-yl)oxy, (pyrrolidin-3-yl)oxy, (1-methylpyrrolidin-3-yl)oxy, (piperidin-3-yl)thio, (piperidin-4-yl)thio, (1-methylpiperidin-3-yl)thio, (1-methylpiperidin-4-yl)thio, (pyrrolidin-3-yl)thio, (1-methylpyrrolidin-2-yl)thio, (piperidin-3-yl)amino, (piperidin-4-yl)amino, (1-methylpiperidin-3-yl)amino, (1-methylpiperidin-4-yl) amino, (pyrrolidin-3-yl) amino and (1-methylpyrrolidin-3-yl)amino.

The present inventive compound can be synthesized, for example, by any of the following processes.

(A) The present inventive compound can be synthesized by reacting a compound of the formula (2):

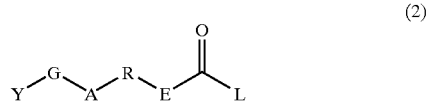

wherein Y, G, A, R and E are as defined above, and L is a hydroxyl group or a leaving group replaceable by a nucleophilic reagent, with guanidine to form a guanidinocarbonyl group (a —C(=O)NHC(=NH)NH$_2$ group), to obtain a compound of the formula (1):

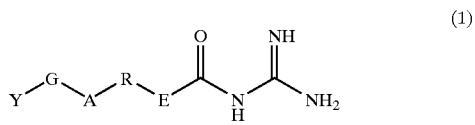

wherein Y, G, A, R and E are as defined above, and if necessary, converting this product to a prodrug thereof or a pharmaceutically acceptable salt of said product or prodrug.

The leaving group replaceable by a nucleophilic reagent includes, for example, halogen atoms (e.g. fluorine, chlorine and bromine), lower alkoxy groups (e.g. methoxy and ethoxy), aralkyloxy groups (e.g. benzyloxy group), aryloxy groups (e.g. phenoxy group), and groups formed by a condensing agent and a compound of the formula (2) in which L is a hydroxyl group. A process for producing the carboxylic acid or reactive derivative thereof of the formula (2) in which L is any of the above-exemplified groups is concretely explained below.

As the carboxylic acid reactive derivative of the formula (2), there may be exemplified acid halides, acid anhydrides (including mixed acid anhydrides) and ester derivatives. Specific examples of the carboxylic acid reactive derivative are acid halides such as acid chlorides and acid bromides; mixed acid anhydrides of an alkyloxycarbonyl chloride (e.g. ethyloxycarbonyl chloride or isobutoxycarbonyl chloride) and an α-polyalkyl-substituted carboxylic acid chloride (e.g. 2-ethyl-n-butyryl chloride or trimethylacetyl chloride); and ester derivatives such as activated esters (e.g. p-nitrophenyl esters, N-hydroxysuccinimide esters and pentafluorophenyl esters) and common esters (e.g. methyl esters and ethyl esters). Such a carboxylic acid reactive derivative can easily be obtained from a corresponding carboxylic acid according to a conventional method.

When guanidine is reacted with the acid halide or the acid anhydride (including the mixed acid anhydride), the reaction may be carried out in a solvent in the presence of a base or excess guanidine with cooling or at room temperature. As the base, there may be exemplified inorganic bases such as sodium hydroxide, potassium hydroxide, sodium carbonate, potassium carbonate, sodium hydrogencarbonate, etc.; and organic bases such as triethylamine, pyridine, etc. As the solvent, there may be exemplified aromatic hydrocarbon solvents such as benzene, toluene, xylene, etc.; ether solvents such as tetrahydrofuran, 1,4-dioxane, etc.; halogenated hydrocarbon solvents such as dichloromethane, chloroform, 1,2-dichloroethane, etc.; amide solvents such as dimethylformamide, dimethylacetamide, etc.; basic solvents such as pyridine, etc.; and mixed solvents thereof.

When guanidine is reacted with the ester derivative, the reaction is carried out in a solvent in the presence of an equimolar or excess amount of guanidine with cooling or heating. When the ester derivative is an activated ester, the reaction is preferably carried out, for example, in an ether solvent (e.g. tetrahydrofuran, 1,2-dimethoxyethane or dioxane), an ester solvent (e.g. ethyl acetate), dimethylformamide, or a mixed solvent thereof. When the ester derivative is other than activated esters, the reaction is preferably carried out, for example, in an alcohol solvent (e.g. methanol, ethanol or isopropanol), an ether solvent (e.g. tetrahydrofuran, 1,2-dimethoxyethane or dioxane), dimethylformamide, or a mixed solvent thereof. After the solvent is distilled off, the residue may be heated for a short time at about 130° C. if necessary.

When there is used a compound of the formula (2) in which L is a hydroxyl group, a compound of the formula (1) can be obtained preferably by reacting the compound of the formula (2) with guanidine in an inert solvent in the presence of a condensing agent at room temperature or with heating.

The reaction is preferably carried out in the presence of a condensing agent [e.g. dicyclohexylcarbodiimide (DCC), diisopropylcarbodiimide (DIPC), 1-ethyl-3-(3-dimethylaminopropyl)-carbodiimide (WSC), benzotriazol-1-yl-tris(dimethylamino)phosphonium hexafluorophosphate (BOP), diphenylphosphonylazide (DPPA), or N,N-carbonyldiimidazole (Angew. Chem. Int. Ed. Engl., Vol. 1, 351(1962))] and optionally an additive [e.g. N-hydroxysuccinimide (HONSu), 1-hydroxybenzotriazole (HOBt) or 3-hydroxy-4-oxo-3,4-dihydro-1,2,3-benzotriazine (HOObt)] in an aromatic hydrocarbon solvent (e.g. benzene, toluene or xylene), an ether solvent (e.g. tetrahydrofuran or 1,4-dioxane), a halogenated hydrocarbon solvent (e.g. dichloromethane, chloroform or 1,2-dichloroethane), an amide solvent (e.g. dimethylformamide or dimethylacetamide), a basic solvent (e.g. pyridine), or a mixed solvent thereof.

(B) A compound of the formula (1) in which G is a group represented by the formula —O— or —N($R^{11}$)—, a prodrug thereof or a pharmaceutically acceptable salt of said compound or prodrug can be synthesized by reacting a compound of the formula (3):

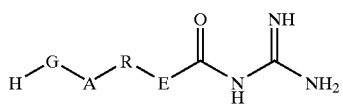

(3)

wherein A, R and E are as defined above, and G is a group represented by the formula —O— or —N($R^{11}$)— wherein $R^{11}$ is as defined above, with sulfur trioxide or a complex thereof to form a sulfo group (a —$SO_3H$ group) on the group G, to obtain a compound of the formula (12):

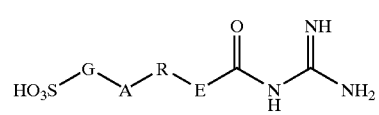

(12)

wherein A, R and E are as defined above, and G is as defined above, and if necessary, converting this product to a prodrug thereof or a pharmaceutically acceptable salt of said product or prodrug.

The reaction is carried out as follows: the compound of the formula (3) is reacted with sulfur trioxide ($SO_3$) or a complex thereof (e.g. a sulfur trioxide-pyridine complex, a sulfur trioxide-dioxane complex, or a sulfur trioxidetrimethylamine complex) in a solvent inert with respect to the reaction (e.g. a halogenated hydrocarbon solvent such as chloroform, methylene chloride or the like, sulfuric acid, pyridine or triethylamine) usually at −30° C. to the boiling point of the solvent, preferably at 0° C. to room temperature.

(A-2) The compound of the formula (2) is well known or may be produced by a combination of well-known processes. It may be produced, for example, by the processes disclosed in the above-mentioned prior art references and the like.

For example, a compound of the formula (2) in which Y is —$SO_3H$ may be produced by reacting a compound of the formula (4):

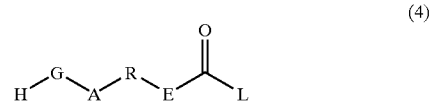

(4)

wherein A, R and E are as defined above and G is a group represented by the formula —O— or —N($R^{11}$)— wherein $R^{11}$ is as defined above, with sulfur trioxide or a complex thereof by a method known in literature (for instance, Organic Functional Group Preparations, second edition; Wasserman, H. H.; Academic Press: London, 1983; Vol. 1, pp. 619–639) or in the same manner as in the above item (B).

As conditions, reagents and the like for the reaction with sulfur trioxide or a complex thereof, there may be exemplified the same conditions, reagents and the like as those described in the above item (B).

(A-3) A compound of the formula (2) in which Y is a group represented by the formula:

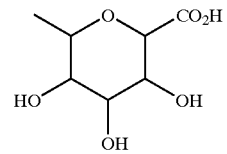

may be produced, for example, by introducing the group represented by the above formula or a group formed by protecting the functional groups of said group either into the compound disclosed in any of the above-mentioned prior art references and the like or in the production process of this compound by a method known in literature (for instance, Shin Jikken Kagaku Koza (New Experimental Chemistry), Vol. 14, "Synthesis and Reaction of Organic Compounds (V)", pp. 2422–2429), and carrying out deprotection at a proper stage.

For example, a compound of the formula (2) in which G is a group represented by the formula —O— or —N($R^{11}$)— and Y is a group represented by the formula:

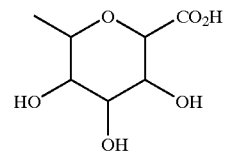

may be produced by reacting a compound of the formula (4):

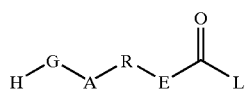
(4)

wherein A, R and E are as defined above and G is a group represented by the formula —O— or —N(R$^{11}$)— wherein R$^{11}$ is as defined above, with a reactive derivative of a compound of the formula (6):

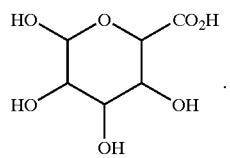
(6)

The compound of the formula (6) includes D-glucuronic acid, L-iduronic acid, L-glucuronic acid, D-mannuronic acid, D-galacturonic acid, etc. Said compound is not limited to these natural uronic acids.

The reaction with the reactive derivative of the compound of the formula (6) may be carried out, for example, as follows: the compound of the formula (4) is reacted with a reactive derivative obtained by protecting the hydroxyl groups and carboxyl group of the above-exemplified compound (a form in which the hydroxyl group is protected includes acetyloxy, benzyloxy, etc., and a form in which the carboxyl group is protected includes a benzyl ester, etc.), for example, an imidate derivative:

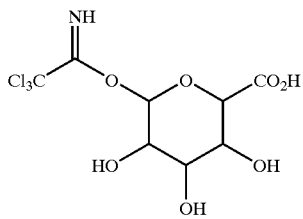

(for instance, imidate derivative of glucuronic acid) (the hydroxyl groups and carboxyl group of the imidate derivative are protected with protective groups (see the above)) according to the so-called imidate method (described, for example, in Helvetica Chimica Acta, 79, 1757–1784 (1996)) in a solvent inert with respect to the reaction (e.g. a halogenated hydrocarbon solvent such as chloroform, methylene chloride or the like) in the presence of a Lewis acid (e.g. a boron trifluoridediethyl ether complex) usually at −30° C. to the boiling point of the solvent, preferably at 0° C. to room temperature.

When the carboxyl group contained in the imidate derivative of compound of the formula (6) is protected, the deprotection of the carboxyl group is preferably carried out at a stage prior to the next step, i.e., the formation of a guanidinocarbonyl group described in the above item (A). When the compound of the formula (4) has a reactive group such as hydroxyl group or amino group in the side chain, the reactive group may be previously protected with a suitable protective group if necessary, and the protective group may be removed after carrying out the reaction.

(B-2) The compound of the formula (3) may be produced by reacting a compound of the formula (4):

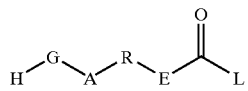
(4)

wherein A, R and E are as defined above and G is a group represented by the formula —O— or —N(R$^{11}$)— wherein R$^{11}$ is as defined above, with guanidine as in the above item (A) to form a guanidinocarbonyl group (a —C(=O)NHC(=NH)NH$_2$ group).

As conditions, reagents and the like for the reaction with guanidine, there may be exemplified the same conditions, reagents and the like as those described in the above item (A).

(C) A compound of the formula (1) in which Y is a group represented by the formula —PO$_3$H$_2$ may be produced, for example, by the following process.

First, a well-known compound or a compound of the formula (5):

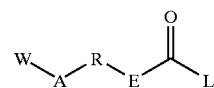
(5)

wherein A, R, E and L are as defined above and W is a halogen atom, a substituted or unsubstituted alkylsulfonyloxy group or a substituted or unsubstituted arylsulfonyloxy group, which may be obtained from a well-known compound by a process known in literature (for example, the process described in the above item (B)), is reacted with a phosphorous acid triester of the formula P(OR$^{41}$)(OR$^{42}$)(OR$^{43}$) or a phosphorous acid diester of the formula HP(=O)(O R$^{42}$)(OR$^{43}$) by a process known in literature (for example, Jikken Kagaku Koza (Experimental Chemistry), 4th edition, Vol. 24, Organic Synthesis VI, pp. 248–249) to form a phosphoric acid diester group (a —P(=O)(O R$^{42}$)(OR$^{43}$) group) at the position of A. In the above formulas, R$^{41}$, R$^{42}$ and R$^{43}$ are independently a substituted or unsubstituted alkyl group. Thus, there is obtained a compound of the formula (6):

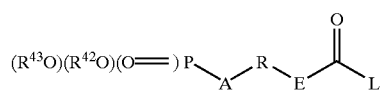
(6)

wherein A, R, E, L, R$^{42}$ and R$^{43}$ are as defined above.

The reaction with the phosphorous acid triester is usually carried out without solvent at a reaction temperature of 100° C. to 200° C. for a reaction time of 1 to 5 hours. The reaction with the phosphorous acid diester is usually carried out in an ether solvent (e.g. tetrahydrofuran) or dimethylformamide in the presence of a base (e.g. potassium tertbutoxide) at a reaction temperature of −20° C. to 30° C. for a reaction time of 1 to 5 hours.

Then, the compound of the formula (6) is reacted with guanidine as in the above item (A) to form a guanidinocarbonyl group (a —C(=O)NHC(=NH)NH$_2$ group), whereby there is obtained a compound of the formula (7):

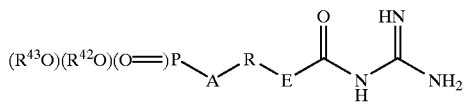

(7)

wherein A, R, E, $R^{42}$ and $R^{43}$ are as defined above. As the reaction conditions, the conditions described in the above item (A) may be exemplified.

Subsequently, a compound of the formula (8):

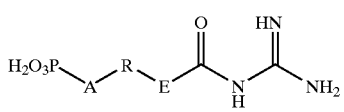

(8)

wherein A, R and E are as defined above, may be produced by removing $R^{42}$ and $R^{43}$ from the compound of the formula (7).

The reaction may be carried out in a halogen-containing solvent (e.g. dichloromethane), acetonitrile or dimethylformamide at a reaction temperature of 20° C. to 100° C. for 1 to 3 days (these reaction conditions are described, for example, in Synthesis 485 (1993)).

A compound of the formula (9):

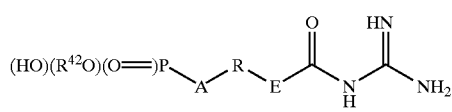

(9)

wherein $R^{42}$, A, R and E are as defined above, may be produced by removing only $R^{43}$ selectively. For example, when a benzyl group is used as $R^{43}$, the compound of the formula (9) may be produced by a conventional benzyl group removing reaction (for example, the method described in Protective Groups in Organic Synthesis, JOHN WILLEY & SONS, 1991).

(D) Each of the compounds of the formula (4) and the formula (3) is well known or may be produced by a combination of well-known processes. It may be produced, for example, by the processes disclosed in the above-mentioned prior art references and the like.

Each of these compounds may be produced by introducing a guanidinocarbonyl group or a group represented by the formula —$SO_3H$ or

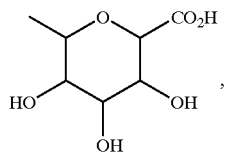

, and synthesizing a basic skeleton, by the above-mentioned method in the course of the production process disclosed in any of the above-mentioned prior art references and the like.

For example, a compound of the formula (4) in which L is a hydroxyl group can easily be derived from a corresponding ester of the formula (4) in which L=$OR_b$, wherein $R_b$ is a lower alkyl group (e.g. methyl or ethyl), an aralkyl group (e.g. benzyl group) or an aryl group (e.g. phenyl), by conventional hydrolysis. A compound of the formula (4) in which L is a leaving group replaceable by a nucleophilic reagent may be synthesized from a compound of the formula (4) in which L is a hydroxyl group, by a conventional method.

When the starting compound in the reaction in each of the production processes described above has a reactive group such as hydroxyl group, amino group or carboxyl group, the reactive group is previously protected with a suitable protective group if necessary, and the protective group is removed after carrying out the reaction or carrying out several reactions, whereby a desired compound may be obtained. As the protective group for the hydroxyl group, amino group or carboxyl group, protective groups conventionally used in the field of organic synthetic chemistry may be used. The introduction and removal of such a protective group may be carried out by a conventional method (for example, Protective Groups in Organic Synthesis, JOHN WILLEY & SONS, 1991).

For example, the protective group for the hydroxyl group includes methoxymethyl group, tetrahydropyranyl group, etc. The protective group for the amino group includes tert-butoxycarbonyl group, etc. Such a protective group for the hydroxyl group may be removed by reaction in a solvent such as aqueous methanol, aqueous ethanol or aqueous tetrahydrofuran in the presence of an acid such as hydrochloric acid, sulfuric acid or acetic acid. The protective group for the amino group may be removed by reaction in a solvent such as aqueous tetrahydrofuran, methylene chloride, chloroform or aqueous methanol in the presence of an acid such as hydrochloric acid or trifluoroacetic acid.

As an enbodyment in which the carboxyl group is protected, there may be exemplified tert-butyl esters, orthoesters and acid amides. The protective group used for this protection is removed as follows. In the case of the tert-butyl esters, the removal is carried out, for example, by reaction in an aqueous solvent in the presence of hydrochloric acid. In the case of the orthoesters, the removal is carried out, for example, by treatment with an acid and then an alkali such as sodium hydroxide in a solvent such as aqueous methanol, aqueous tetrahydrofuran or aqueous 1,2-dimethoxyethane. In the case of the acid amides, the removal may be carried out, for example, by reaction in a solvent such as water, aqueous methanol or aqueous tetrahydrofuran in the presence of an acid such as hydrochloric acid or sulfuric acid.

The compound of the formula (1) has the acylguanidine moiety shown in the above formula (1) and has tautomers. In detail, there are a tautomer [—C(=O)N=C(NH$_2$)$_2$] whose acylguanidine moiety is diaminomethyleneamino, and another tautomer [—C(=O)NH—C(=NH)NH$_2$] whose acylguanidine moiety is aminoiminomethylamino. These tautomers are different only in state and are the same compound. Therefore, the present invention includes both of the tautomers.

The compound of the formula (1) includes those having an optical center of asymmetry. The compound having an optical center of asymmetry may be obtained as a racemic modification, or it may be obtained as an optically active substance when an optically active starting material is used. If necessary, the recemic modification obtained may be physically or chemically resolved into optical antipodes by a conventional method. Preferably, diastereomers are formed from the racemic mixture by a reaction using a reagent for optical resolution. The diastereomers different in form may be resolved by a conventional method such as fractional crystallization.

As the "prodrug", there may be exemplified those which are easily hydrolyzed in a living body to regenerate the compound of the formula (1). For example, when the compound of the formula (1) has a carboxyl group, examples of the prodrug are compounds obtained by converting the carboxyl group to an alkoxycarbonyl group, an alkylthiocarbonyl group or an alkylaminocarbonyl group.

For example, when the compound of the formula (1) has an amino group, examples of the prodrug are compounds obtained by converting the amino group to an alkanoylamino group by substitution by the alkanoyl group, compounds obtained by converting the amino group to an alkoxycarbonylamino group by substitution by the alkoxycarbonyl group, and compounds obtained by converting the amino group to an acyloxymethylamino group or hydroxylamine.

For example, when the compound of the formula (1) has a hydroxyl group, examples of the prodrug are compounds obtained by converting the hydroxyl group to an acyloxy group by substitution by the above-exemplified acyl group, and compounds obtained by converting the hydroxyl group to a phosphoric ester or an acyloxymethyloxy group.

For example, when the compound of the formula (1) has a sulfo group, examples of the prodrug are compounds obtained by converting the sulfo group to a sulfonic ester by substitution by an alkyl group.

For example, when the compound of the formula (1) has a phosphono group, examples of the prodrug are compounds obtained by converting the phosphono group to a phosphonic acid monoester or a phosphonic acid diester by substitution by one or two alkyl groups.

Examples of the alkyl portion of the group used for such conversion to the prodrug are the above-exemplified alkyl groups. The alkyl group may be substituted by, for example, an alkoxy group of 1 to 6 carbon atoms. Preferable examples of the group formed for the above conversion to the prodrug are as follows.

(a) For example, in the case of compounds obtained by converting the carboxyl group to an alkoxycarbonyl group, the alkoxycarbonyl group includes, for example, lower (number of carbon atoms: for example, 1 to 6) alkoxycarbonyl groups such as methoxycarbonyl, ethoxycarbonyl, etc.; lower (number of carbon atoms: for example, 1 to 6) alkoxycarbonyl groups substituted by a lower (number of carbon atoms: for example, 1 to 6) alkoxy group, such as methoxymethoxycarbonyl, ethoxymethoxycarbonyl, 2-methoxyethoxycarbonyl, 2-methoxyethoxymethoxycarbonyl, pivaloyloxymethoxycarbonyl, etc.; lower (number of carbon atoms: for example, 1 to 6) alkoxycarbonyl groups substituted by a lower (number of carbon atoms: for example, 1 to 6) alkoxycarbonyloxy group, such as 1-(ethoxycarbonyloxy)ethyl; (1,3-dihydro-3-oxo-1-isobenzofuranyl)oxycarbonyl; and (5-methyl-2-oxo-1,3-dioxolen-4-yl)methoxycarbonyl.

(b) For example, in the case of compounds obtained by converting the sulfo group to an alkoxysulfonyl group, the alkoxysulfonyl group includes lower (number of carbon atoms: for example, 1 to 6) alkoxysulfonyl groups such as methoxysulfonyl, ethoxysulfonyl, etc.; and lower (number of carbon atoms: for example, 1 to 6) alkoxysulfonyl groups substituted by a lower (number of carbon atoms: for example, 1 to 6) alkoxy group, such as methoxymethoxysulfonyl, ethoxymethoxysulfonyl, 2-methoxyethoxysulfonyl, 2-methoxyethoxymethoxysulfonyl, pivaloyloxymethoxysulfonyl, etc.

(c) For example, in the case of compounds obtained by converting the phosphono group to an alkoxyphosphoryl group, the alkoxyphosphoryl group includes lower (number of carbon atoms: for example, 1 to 6) mono- or dialkoxyphosphoryl groups such as methoxy(hydroxy)phosphoryl, ethoxy(hydroxy)phosphoryl, dimethoxyphosphoryl, diethoxyphosphoryl, etc.; and lower (number of carbon atoms: for example, 1 to 6) mono- or dialkoxyphosphoryl groups substituted by a lower (number of carbon atoms: for example, 1 to 6) alkoxy group, such as methoxymethoxy(hydroxy)-phosphoryl, ethoxymethoxy(hydroxy)phosphoryl, 2-methoxyethoxy(hydroxy)phosphoryl, 2-methoxyethoxymethoxy(hydroxy)phosphoryl, pivaloyloxymethoxy(hydroxy)phosphoryl, bis(methoxymethoxy)phosphoryl, bis(ethoxymethoxy)phosphoryl, bis(2-methoxyethoxy)phosphoryl, bis(pivaloyloxymethoxy)phosphoryl, etc.

If necessary, the compound of the formula (1) or the prodrug thereof may be converted to a pharmaceutically acceptable salt. As such a salt, there may be exemplified salts with mineral acids such as hydrochloric acid, hydrobromic acid, sulfuric acid, phosphoric acid, etc.; salts with organic carboxylic acids such as formic acid, acetic acid, fumaric acid, maleic acid, oxalic acid, citric acid, malic acid, tartaric acid, aspartic acid, glutamic acid, etc.; salts with sulfonic acids such as methanesulfonic acid, benzenesulfonic acid, p-toluenesulfonic acid, hydroxybenzenesulfonic acid, dihydroxybenzenesulfonic acid, etc.; alkali metal salts such as sodium salt, potassium salt, etc.; alkaline earth metal salts such as calcium salt, magnesium salt, etc.; ammonium salt; triethylamine salt; pyridine salt; picoline salt; ethanolamine salt; dicyclohexylamine salt; and N,N'-dibenzylethylenediamine salt.

Each of the compounds of the formula (1), the prodrugs thereof and the pharmaceutically acceptable salts of the compounds or prodrugs may be in the form of an anhydride, hydrate or solvate.

When used as a pharmaceutical composition, the present inventive compound may be orally or parenterally administered. That is, the present inventive compound may be orally administered in a usual dosage form such as powder, granules, tablets, capsules, syrup, suspension or the like, or the present inventive compound may be parenterally administered, for example, by injection of a solution, emulsion or suspension prepared from the present inventive compound. The present inventive compound may be administered rectally in the form of a suppository. The present inventive compound may be formulated into the above-exemplified suitable dosage form by blending the present inventive compound with conventional acceptable adjuvants such as a carrier, excipient, binder, stabilizer and diluent. When the present inventive compound is used in the form of an injection, the injection may contain acceptable additives such as a buffer, solubilizer and tonicity agent. Although the dose and the number of administrations are varied depending on, for example, a disease to be cured, the condition of the disease, age, body weight and administration route, the present inventive compound may be administered to an adult in a dose of usually 0.1 to 2,000 mg, preferably 1 to 200 mg per day in one portion or several portions (for example, 2 to 4 portions).

In the present invention, as more preferable compounds, there may be exemplified compounds represented by the formula:

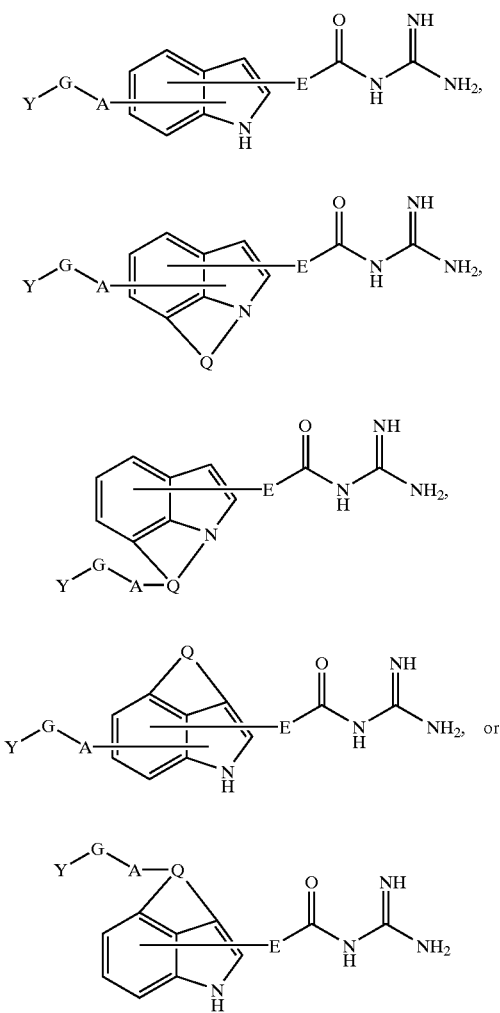

wherein Y, G, A and E are as defined above;

Q is a substituted or unsubstituted lower alkylene group (one or more of the —CH$_2$— groups of said lower alkylene group may be replaced by one or more substituents, respectively, which may be the same or different and are selected from groups represented by the formula —O—, —S—, —N(R$^{31}$)— and —C(=O)— (as R$^{31}$, there may be exemplified the same groups as those exemplified above as R$^1$), and any two adjacent atoms of said lower alkylene group may form a double bond or a triple bond);

the group represented by the formula —E—C(=O)NHC(=NH)NH$_2$ in each of the above formulas may be bonded to any acceptable position of the indole ring, the group represented by the formula Y—G—A— in each of the formulas (31), (32) and (34) may be bonded to any acceptable position of the indole ring, and the group represented by the formula Y—G—A— in each of the formulas (33) and (35) may be a substituent on Q, preferably on the carbon atom of Q, prodrugs of said compounds, and pharmaceutically acceptable salts of said compounds and prodrugs.

In the formulas (31) to (35), the polycyclic heterocyclic rings may be substituted by any of the above-exemplified substituents of polycyclic heterocyclic ring, inclusive of the hydrogen atom of the group represented by the formula —NH— in the ring.

The present invention is more concretely illustrated below with examples and test examples, which should not be construed as limiting the scope of the invention. The nomenclature of compounds shown in the examples mentioned below is not always based on IUPAC.

EXAMPLE 1

Synthesis of 2-[[[amino(imino)methyl]amino]-carbonyl]-1,4-dimethyl-1H-indol-5-yl Hydrogen Sulfate (N-(aminoiminomethyl)-1,4-dimethyl-5-(hydroxysulfonyloxy)-1H-indole-2-carboxamide)

(a) Synthesis of Ethyl 5-benzyloxy-1,4-dimethyl-1H-indole-2-carboxylate

A mixture of ethyl 5-benzyloxy-4-methyl-1H-indole-2-carboxylate (3.50 g, 11.3 mmol), 60% sodium hydride (0.45 g, 11.3 mmol) and N,N-dimethylformamide (70 ml) was stirred at room temperature for 30 minutes, and then methyl iodide (3.21 g, 22.6 mmol) was added dropwise thereto, followed by stirring at room temperature for another 2.5 hours. The reaction mixture was poured into a 5% aqueous sodium chloride solution and extracted twice with ethyl acetate, and the extract solution was washed with a 5% aqueous sodium chloride solution and then dried over anhydrous magnesium sulfate. The solvent was distilled off under reduced pressure and the resulting residue was purified by a silica gel column chromatography (eluent:ethyl acetate/n-hexane=3/97) to obtain 3.53 g of ethyl 5-benzyloxy-1,4-dimethyl-1H-indole-2-carboxylate.

Melting point: 100–101° C.

(b) Synthesis of Ethyl 1,4-dimethyl-5-hydroxy-1H-indole-2-carboxylate

A mixture of ethyl 5-benzyloxy-1,4-dimethyl-1H-indole-2-carboxylate (4.00 g, 12.4 mmol), ammonium formate (3.90 g, 61.8 mmol), 10% palladium/carbon (0.20 g) and ethanol (60 ml) was stirred at 60° C. for 1.5 hours. The catalyst was filtered off and the resulting filtrate was concentrated under reduced pressure. A 5% aqueous sodium chloride solution was added to the resulting residue, followed by extraction with ethyl acetate. The extract solution was washed with a 5% aqueous sodium chloride solution and then dried over anhydrous magnesium sulfate. The solvent was distilled off under reduced pressure to obtain 2.89 g of ethyl 1,4-dimethyl-5-hydroxy-1H-indole-2-carboxylate.

(c) Synthesis of 2-ethoxycarbonyl-1,4-dimethyl-1H-indol-5-yl Hydrogen Sulfate Pyridine Salt (Ethyl 1,4-dimethyl-5-(hydroxysulfonyloxy)-1H-indole-2-carboxylate Pyridine Salt)

A sulfur trioxide-pyridine complex (SO$_3$—Py; 4.36 g, 27.4 mmol) was added to a solution of ethyl 1,4-dimethyl-5-hydroxy-1H-indole-2-carboxylate (2.13 g, 9.13 mmol) in pyridine (35 ml), and the resulting mixture was stirred at room temperature for 3 hours. The solvent was distilled off under reduced pressure and water was added to the resulting residue, followed by washing with diethyl ether (three times). The solid thus precipitated was collected by filtration and dried under reduced pressure to obtain 3.20 g of 2-ethoxycarbonyl-1,4-dimethyl-1H-indol-5-yl hydrogen sulfate pyridine salt.

(d) Synthesis of 2-[[[amino(imino)methyl]-amino]carbonyl]-1,4-dimethyl-1H-indol-5-yl Hydrogen Sulfate A mixture of sodium methoxide (4.28 g, 79.2 mmol), guanidine hydrochloride (7.58 g, 79.3 mmol) and N,N-dimethylformamide (70 ml) was stirred at room temperature for 1 hour, and then the insoluble material was filtered off.

A solution of 2-ethoxycarbonyl-1,4-dimethyl-1H-indole-5-yl hydrogen sulfate pyridine salt (3.11 g, 7.92 mmol) in N,N-dimethylformamide (10 ml) was added to the filtrate, and the resulting mixture was stirred at room temperature for 7.5 hours. Water was added to the reaction mixture, followed by washing with chloroform. Subsequently, chloroform and then 2N hydrochloric acid were added and the solid thus precipitated was collected by filtration and washed with methanol to obtain 2.12 g of 2-[[[amino(imino)-methyl]amino]carbonyl]-1,4-dimethyl-1H-indol-5-yl hydrogen sulfate.

Melting point: 267–268° C. (decomp.).

MS (FAB+) (m/z): 327 (M+H$^+$).

The following compounds of Example 2 and Example 3 were synthesized according to the process described in Example 1.

EXAMPLE 2

2-[[[Amino(imino)methyl]amino]carbonyl]-1,4-dimethyl-1H-indol-6-yl Hydrogen Sulfate Melting point: 303–304° C. (decomp.).

EXAMPLE 3

2-[[[Amino(imino)methyl]amino]carbonyl]-1-methyl-1H-indol-7-yl Hydrogen Sulfate

Melting point: 279–280° C. (decomp.).

EXAMPLE 4

Synthesis of 2-[[[amino(imino)methyl]amino]-carbonyl]-1,4-dimethyl-1H-indol-7-yl Hydrogen Sulfate (N-(aminoiminomethyl)-1,4-dimethyl-7-(hydroxysulfonyloxy)-1H-indole-2-carboxamide)

(a) Synthesis of N-(aminoiminomethyl)-1,4-dimethyl-7-hydroxy-1H-indole-2-carboxamide Methanesulfonate Reaction was carried out according to the method described in Example 1, (d), except for using ethyl 1,4-dimethyl-7-hydroxy-1H-indole-2-carboxylate (see Reference Example 21 in Japanese Patent Unexamined Publication No. 8-208602) as a starting material. Then, the reaction product was converted to a methanesulfonate in aqueous 2-propanol to obtain N-(aminoiminomethyl)-1,4-dimethyl-7-hydroxy-1H-indole-2-carboxamide methanesulfonate.

Melting point: 259–260° C. (decomp.).

(b) Synthesis of 2-[[[amino(imino)methyl]-amino]carbonyl]-1,4-dimethyl-1H-indol-7-yl Hydrogen Sulfate A sulfur trioxide-pyridine complex (2.51 g, 15.8 mmol) was added to a solution of N-(aminoiminomethyl)-1,4-dimethyl-7-hydroxy-1H-indole-2-carboxamide methanesulfonate (1.80 g, 5.26 mmol) in pyridine (20 ml), and the resulting mixture was stirred at room temperature for 16.5 hours. The solvent was distilled off under reduced pressure and water was added to the residue. Subsequently, diethyl ether was added thereto, and the solid precipitated was collected by filtration and washed with methanol to obtain 1.43 g of 2-[[[amino(imino)methyl]amino]carbonyl]-1,4-dimethyl-1H-indol-7-yl hydrogen sulfate.

Melting point: >315° C. (decomp.).

MS (FAB+) (m/z): 327 (M+H$^+$).

The following compounds of Examples 5 to 7 were synthesized according to the process described in Example 4.

EXAMPLE 5

2-[[[Amino(imino)methyl]amino]carbonyl]-1-methyl-1H-indol-4-yl Hydrogen Sulfate

Melting point: 249–250° C. (decomp.).

EXAMPLE 6

2-[[[Amino(imino)methyl]amino]carbonyl]-1-methyl-1H-indol-5-yl Hydrogen Sulfate

Melting point: 280–281° C. (decomp.).

EXAMPLE 7

2-[[[Amino(imino)methyl]amino]carbonyl]-1-methyl-1H-indol-6-yl Hydrogen Sulfate

Melting point: 283–284° C. (decomp.).

EXAMPLE 8

Synthesis of [2-[[[amino(imino)methyl]amino]-carbonyl]-1-methyl-1H-indol-6-yl] β-D-glucopyranosideuronic Acid Methanesulfonate (a) Synthesis of Benzyl [(2-ethoxycarbonyl-1-methyl-1H-indol-6-yl) 2,3,4-tri-O-acetyl-β-D-glucopyranoside]uronate A mixture of ethyl 6-hydroxy-1-methyl-1H-indole-2-carboxylate (0.77 g, 3.50 mmol), benzyl 2,3,4,-tri-O-acetyl-D-glucopyranosyluronate trichloroacetoimidate (2.33 g, 4.20 mmol; synthesized according to the process described in Helvetica Chimica Acta, 79, 1757 (1996); and called 2,3,4-tri-O-acetyl-5-C-benzyloxycarbonyl-α/β-D-glucopyranosyltrichloroacetoimidate according to the nomenclature followed in the case of the compound described in the reference), molecular sieves 3A (5.0 g) and methylene chloride (20 ml) was stirred at room temperature for 1 hour and then cooled to −20° C. Subsequently, a boron trifluoridediethyl ether complex (89 μl, 0.70 mmol) was added to the reaction mixture, and the resulting mixture was stirred at −20° C. for another 2 hours. The mixture stirred was diluted with ethyl acetate and quenched with a small volume of a saturated aqueous sodium hydrogencarbonate solution. After the insoluble material was filtered off, the filtrate was extracted with ethyl acetate and the extract solution was washed with a saturated aqueous sodium chloride solution and dried over anhydrous sodium sulfate. The solvent was distilled off under reduced pressure and the resulting residue was purified by a silica gel column chromatography (eluent; ethyl acetate:n-hexane=1:2) to obtain 2.14 g of benzyl [(2-ethoxycarbonyl-1-methyl-1H-indol-6-yl) 2,3,4-tri-O-acetyl-β-D-glucopyranoside]uronate.

(b) Synthesis of (2-ethoxycarbonyl-1-methyl-1H-indol-6-yl) 2,3,4-tri-O-acetyl-β-D-glucopyranosideuronic Acid Benzyl [(2-ethoxycarbonyl-1-methyl-1H-indol-6-yl) 2,3,4-tri-O-acetyl-β-D-glucopyranoside]uronate (2.08 g, 3.40 mmol) was dissolved in a mixture of ethyl acetate (30 ml) and ethanol (30 ml), followed by adding thereto 10% palladium-carbon (0.21 g), and the resulting mixture was stirred under a hydrogen atmosphere for 30 minutes. The catalyst was filtered off and the resulting residue was concentrated under reduced pressure to obtain 1.75 g of (2-ethoxycarbonyl-1-methyl-1H-indol-6-yl) 2,3,4-tri-O-acetyl-β-D-glucopyranosideuronic acid.

(c) Synthesis of [2-[[[amino(imino)methyl]amino]-carbonyl]-1-methyl-1H-indol-6-yl] β-D-glucopyranosideuronic Acid Methanesulfonate Guanidine hydrochloride (6.23 g, 65.2 mmol) was added to a mixture of sodium methoxide (3.52 g, 65.2 mmol) and N,N-dimethylformamide (25 ml), and the resulting mixture was stirred at room temperature for 1 hour. The solid precipitated was filtered off and a solution of (2-ethoxycarbonyl-1-methyl-1H-indol-6-yl) 2,3,4-tri-O-acetyl-β-D-glucopyranosideuronic acid (1.70 g, 3.26 mmol) in N,N-dimethylformamide (9 ml) was added to the filtrate obtained, followed by stirring at room temperature for 7 hours. After toluene was added to the reaction mixture, the resulting mixture was concentrated under reduced pressure, and the resulting residue was purified by a reversed phase column chromatography (eluent; water:methanol=9:1) to obtain a free compound. The free compound was dissolved in water (50 ml) and methanesulfonic acid (1.15 g) was added thereto under ice-cooling. Subsequently, the solvent was distilled off under reduced pressure and the resulting residue was washed with tetrahydrofuran to obtain 0.78 g of [2-[[[amino(imino)methyl]amino]carbonyl]-1-methyl-1H-indol-6-yl] β-D-glucopyranosideuronic acid methanesulfonate.

Melting point: 170–171° C.
MS (FAB+) (m/z): 409 (M+H$^+$).

The following compounds of Example 9 and Example 10 were synthesized by the same process as in Example 8.

EXAMPLE 9

[2-[[[Amino(imino)methyl]amino]carbonyl]-1-methyl-1H-indol-5-yl] β-D-glucopyranosideuronic Acid Methanesulfonate Melting point: 219° C. (decomp.).
MS (FAB+) (m/z): 409 (M+H$^+$).

EXAMPLE 10

[2-[[[Amino(imino)methyl]amino]carbonyl]-1,4-dimethyl-1H-indol-5-yl] γ-D-glucopyranosideuronic Acid Methanesulfonate Melting point: 169–170° C.
MS (FAB+) (m/z): 423 (M+H$^+$).

The following compounds of Examples 11 to 14 were synthesized by the same process as in Example 1.

EXAMPLE 11

2-[[[Amino(imino)methyl]amino]carbonyl]-4-chloro-1-methyl-1H-indol-6-yl Hydrogen Sulfate Melting point: 298° C. (decomp.).

EXAMPLE 12

2-[[[Amino(imino)methyl]amino]carbonyl]-1-methyl-4-(trifluoromethyl)-1H-indol-6-yl Hydrogen Sulfate Melting point: 300° C. (decomp.).

EXAMPLE 13

2-[[[Amino(imino)methyl]amino]carbonyl]-1-methyl-4-(trifluoromethyl)-1H-indol-7-yl Hydrogen Sulfate Melting point: 298° C. (decomp.).

EXAMPLE 14

2-[[[Amino(imino)methyl]amino]carbonyl]-4-chloro-1-methyl-1H-indol-7-yl Hydrogen Sulfate Melting point: 338° C. (decomp.).

EXAMPLE 15

Synthesis of [2-[[[amino(imino)methyl]amino]-carbonyl]-1-methyl-4-(trifluoromethyl)-1H-indol-6-yl]-methylphosphonic Acid
(a) Synthesis of Ethyl 1-methyl-4-(trifluoromethyl)-6-[[(trifluoromethyl)sulfonyl]oxy]-1H-indole-2-carboxylate Under nitrogen, ethyl 6-hydroxy-1-methyl-4-(trifluoromethyl)-1H-indole-2-carboxylate (1.50 g, 5.22 mmol) was dissolved in dichloromethane (30 ml), and triethylamine (1.46 ml, 10.44 mmol) was added thereto. The resulting mixture was cooled to −16° C., followed by adding dropwise thereto trifluoromethanesulfonic acid anhydride (0.97 ml, 5.74 mmol), and the mixture thus obtained was stirred for 30 minutes while maintaining the temperature.

Water was added to the reaction mixture, followed by extraction with chloroform. The organic layer was washed with water and then a saturated aqueous sodium chloride solution, dried over anhydrous magnesium sulfate, filtered, and then distilled under reduced pressure to remove the solvent, whereby 2.14 g of ethyl 1-methyl-4-(trifluoromethyl)-6-[[(trifluoromethyl)sulfonyl]oxy]-1H-indole-2-carboxylate was obtained as a skin-colored solid.

Melting point: 98–103° C.
(b) Synthesis of Ethyl 1-methyl-4-(trifluoromethyl)-6-vinyl-1H-indole-2-carboxylate Under nitrogen, ethyl 1-methyl-4-(trifluoromethyl)-6-[[(trifluoromethyl)sulfonyl]oxy]-1H-indole-2-carboxylate (2.92 g, 6.96 mmol) was dissolved in dimethylformamide (60 ml), and tributylvinyltin (2.44 ml, 8.36 mmol) and lithium chloride (0.886 g, 0.89 mmol) were added thereto and stirred for 30 minutes. Thereafter, dichlorobis-(triphenylphosphine)palladium(II) (0.244 g, 0.348 mmol) was added thereto.

The resulting mixture was stirred at room temperature for 1 hour, stirred for 30 minutes while being maintained at 70° C., and then cooled to room temperature. Water was added to the reaction mixture, followed by extraction with a 1:1 mixture of toluene and ethyl acetate. The extract layer was washed with water and then a saturated aqueous sodium chloride solution, dried over anhydrous magnesium sulfate and Carborafin, filtered, and then distilled under reduced pressure to remove the solvent. The concentrated residue thus obtained was purified by a silica gel column chromatography (eluent: n-hexane/ethyl acetate=40/1 and 30/1) to obtain 2.02 g of ethyl 1-methyl-4-(trifluoromethyl)-6-vinyl-1H-indole-2-carboxylate as white crystals.
(c) Synthesis of Ethyl 6-formyl-1-methyl-4-(trifluoromethyl)-1H-indole-2-carboxylate Under nitrogen, ethyl 1-methyl-4-(trifluoromethyl)-6-vinyl-1H-indole-2-carboxylate (1.00 g, 3.36 mmol) was dissolved in tetrahydrofuran (20 ml), and water (10 ml) and potassium osmate(VI) dihydrate (124 mg, 0.336 mmol) were added thereto. A solution of sodium periodate (791 mg, 3.92 mmol) in water (10 ml) was added dropwise thereto over a period of 20 minutes, and the resulting mixture was stirred at room temperature for 5 hours.

An aqueous sodium thiosulfate solution was added to the reaction mixture and stirred, followed by extraction with ethyl acetate. The extract layer was washed with water and then a saturated aqueous sodium chloride solution, dried over anhydrous magnesium sulfate, filtered, and then distilled under reduced pressure to remove the solvent. The concentrated residue thus obtained was purified by a silica gel column chromatography (eluent: n-hexane/ethyl acetate=10/1, 8/1 and 5/1) to obtain 0.68 g of ethyl 6-formyl-1-methyl-4-(trifluoromethyl)-1H-indole-2-carboxylate as a white solid.

Melting point: 140–141° C.
(d) Synthesis of Ethyl 6-(hydroxymethyl)-1-methyl-4-(trifluoromethyl)-1H-indole-2-carboxylate Under nitrogen, ethyl 6-formyl-1-methyl-4-(trifluoromethyl)-1H-indole-2-carboxylate (600 mg, 2.01 mmol) was dissolved in ethanol (30 ml), followed by adding thereto sodium tetrahydroborate (76 mg, 2.01 mmol) under ice-cooling, and the resulting mixture was stirred under ice-cooling for 30 minutes.

The reaction mixture was adjusted to pH 1 with a 1N aqueous hydrochloric acid solution while taking care to prevent bubbling, and was extracted twice with ethyl acetate. The combined extract layer was washed with water and then a saturated aqueous sodium chloride solution, dried over anhydrous magnesium sulfate, filtered, and then distilled under reduced pressure to remove the solvent, whereby 593 mg of ethyl 6-(hydroxymethyl)-1-methyl-4-(trifluoromethyl)-1H-indole-2-carboxylate was obtained as a white solid.

Melting point: 158–159° C.

(e) Synthesis of Ethyl 6-(bromomethyl)-1-methyl-4-(trifluoromethyl)-1H-indole-2-carboxylate Under nitrogen, ethyl 6-(hydroxymethyl)-1-methyl-4-(trifluoromethyl)-1H-indole-2-carboxylate (550 mg, 2.82 mmol) and then triphenylphosphine (575 mg, 2.19 mmol) were dissolved in dichloromethane (30 ml), followed by adding thereto carbon tetrabromide (908 mg, 2.74 mmol), and the resulting mixture was stirred at room temperature for 2.5 hours.

The reaction mixture was adjusted to pH 9 with a saturated aqueous sodium hydrogencarbonate solution, stirred and then separated. The dichloromethane layer was washed with a saturated aqueous sodium chloride solution, dried over anhydrous magnesium sulfate, filtered, and then distilled under reduced pressure to remove the solvent. The concentrated residue thus obtained was purified by a silica gel column chromatography (eluent: n-hexane/ethyl acetate=20/1, 15/1, 10/1, 5/1, 3/1 and 2/1) to obtain 553 mg of ethyl 6-(bromomethyl)-1-methyl-4-(trifluoromethyl)-1H-indole-2-carboxylate as a white solid.

Melting point: 139–141° C.

(f) Synthesis of Ethyl 6-[(diethoxyphosphoryl)methyl]-1-methyl-4-(trifluoromethyl)-1H-indole-2-carboxylate Under nitrogen, triethyl phosphite (589 µl, 3.43 mmol) was added to ethyl 6-(bromomethyl)-1-methyl-4-(trifluoromethyl)-1H-indole-2-carboxylate (250 mg, 0.687 mmol), and the resulting mixture was stirred for 2 hours while being maintained at 140° C. The excess triethyl phosphite was distilled off as much as possible, and the resulting concentrated residue was purified by a silica gel column chromatography (eluent: n-hexane/ethyl acetate=15/1, 10/1, 3/1, 1/1, 1/4 and 0/10) to obtain 276 mg of ethyl 6-[(diethoxyphosphoryl)methyl]-1-methyl-4-(trifluoromethyl)-1H-indole-2-carboxylate as a white solid.

Melting point: 95–96.5° C.

(g) Synthesis of Diethyl [2-[[[amino(imino)methyl]-amino]carbonyl]-1-methyl-4-(trifluoromethyl)-1H-indol-6-yl]methylphosphonate Under nitrogen, sodium methoxide (321 mg, 5.93 mmol) was suspended in dimethylformamide (4 ml), followed by adding thereto guanidine hydrochloride (567 mg, 5.93 mmol), and the resulting mixture was stirred at room temperature for 1 hour.

Separately, ethyl 6-[(diethoxyphosphoryl)-methyl]-1-methyl-4-(trifluoromethyl)-1H-indole-2-carboxylate (250 mg, 0.593 mmol) was dissolved in dimethylformamide (2 ml), followed by adding thereto the guanidine solution previously prepared, and the resulting mixture was stirred at room temperature for 2.5 hours.

The reaction mixture was adjusted to pH 10 by addition of water and extracted twice with a 1:3 mixture of toluene and ethyl acetate. The combined extract layer was washed twice with water and then once with a saturated aqueous sodium chloride solution, dried over anhydrous magnesium sulfate, filtered, and then distilled under reduced pressure to remove the solvent. To the concentrated residue thus obtained were added chloroform (1 ml) and diethyl ether to effect crystallization. The white crystals were collected by filtration, washed with diethyl ether, and then dried under reduced pressure to obtain 173 mg of diethyl [2-[[[amino(imino)methyl]amino]carbonyl]-1-methyl-4-(trifluoromethyl)-1H-indol-6-yl]methylphosphonate as a white solid.

Melting point: 162–163° C.

(h) Synthesis of [2-[[[amino(imino)methyl]amino]-carbonyl]-1-methyl-4-(trifluoromethyl)-1H-indol-6-yl] methylphosphonic Acid Hydrobromide Under nitrogen, diethyl [2-[[[amino(imino)-methyl]amino]carbonyl]-1-methyl-4-(trifluoromethyl)-1H-indol-6-yl]methylphosphonate (163 mg, 0.375 mmol) was dissolved in dichloromethane (1.5 ml), and bromotrimethylsilane (173 µl, 1.31 mmol) was added thereto.

After the resulting mixture was stirred at room temperature for 3 days (two 173-µl portions of bromotrimethylsilane were added during the stirring), the mixture was concentrated to dryness under reduced pressure. The concentrate was suspended in a mixture of dichloromethane (3 ml) and methanol (2 ml), and the suspension was concentrated to dryness under reduced pressure. The resulting concentrated residue was sufficiently suspended in isopropyl alcohol (2 ml), followed by adding thereto a small volume of a 25% solution of hydrogen bromide in acetic acid, and diethyl ether was added thereto to effect sufficient dispersion. Then, the crystals were collected by filtration, washed with diethyl ether, and then dried under reduced pressure to obtain 168 mg of [2-[[[amino(imino)methyl]amino]carbonyl]-1-methyl-4-(trifluoromethyl)-1H-indol-6-yl] methylphosphonic acid hydrobromide as a white solid.

Melting point: 274–285° C. (decomp.).

(i) Synthesis of [2-[[[amino(imino)methyl]amino]-carbonyl]-1-methyl-4-(trifluoromethyl)-1H-indol-6-yl] methylphosphonic Acid

[2-[[[Amino(imino)methyl]amino]carbonyl]-1-methyl-4-(trifluoromethyl)-1H-indol-6-yl]methylphosphonic acid hydrobromide (1.37 g, 2.87 mmol) was suspended in distilled water (50 ml), followed by adding thereto a 1.0N aqueous sodium hydroxide solution (8.62 ml, 8.62 mmol) to effect dissolution and adjust the pH to about 11, and the insoluble material was removed by filtration. The filtrate was adjusted to pH 5 to 6 with a 1.0N aqueous hydrochloric acid solution (5.75 ml, 5.75 mmol), and the white solid precipitated was collected by filtration. The white solid obtained was washed with water and then dried under reduced pressure to obtain 1.10 g of [2-[[[amino(imino)methyl]-amino]carbonyl]-1-methyl-4-(trifluoromethyl)-1H-indol-6-yl]methyl-phosphonic acid as a white solid.

Melting point: 231–266° C. (decomp.).

MS (ESI) (m/z): 379 (M+H$^+$).

The following compounds of Examples 16 to 20 were synthesized according to the process described in Example 15.

EXAMPLE 16

[2-[[[Amino(imino)methyl]amino]carbonyl]-1-methyl-4-(trifluoromethyl)-1H-indol-7-yl]methylphosphonic Acid Melting point: 249–265° C. (decomp.).

MS (ESI) (m/z): 379 (M+H$^+$).

EXAMPLE 17

[2-[[[Amino(imino)methyl]amino]carbonyl]-4-chloro-1-methyl-1H-indol-6-yl]methylphosphonic Acid Melting point: 265–282° C. (decomp.).

MS (ESI) (m/z): 345 (M+H$^+$).

EXAMPLE 18

[2-[[[Amino(imino)methyl]amino]carbonyl]-4-chloro-1-methyl-1H-indol-7-yl]methylphosphonic Acid Melting point: 273–284° C. (decomp.).

MS (ESI) (m/z): 345 (M+H$^+$).

EXAMPLE 19

[2-[[[Amino(imino)methyl]amino]carbonyl-1,4-dimethyl-1H-indol-6-yl]methylphosphonic Acid Melting point: 229–288° C. (decomp.).

MS (ESI) (m/z): 325 (M+H$^+$).

EXAMPLE 20

[2-[[[Amino(imino)methyl]amino]carbonyl]-1,4-dimethyl-1H-indol-7-yl]methylphosphonic Acid Melting point: 239–280° C. (decomp.).

MS (ESI) (m/z): 325 (M+H$^+$).

EXAMPLE 21

Synthesis of [[2-[[[amino(imino)methyl]-amino]carbonyl]-1-methyl-4-(trifluoromethyl)-1H-indol-6-yl]oxy]acetic Acid (a) Synthesis of Ethyl 6-(2-tert-butoxy-2-oxoethoxy)-1-methyl-4-(trifluoromethyl)-1H-indole-2-carboxylate Under nitrogen, ethyl 6-hydroxy-1-methyl-4-(trifluoromethyl)-1H-indole-2-carboxylate (1.0 g, 3.48 mmol) was dissolved in dimethylformamide (10 ml), and potassium carbonate (0.722 g, 5.22 mmol) was suspended therein. Then, tert-butyl bromoacetate (0.565 ml, 3.83 mmol) was added thereto and the resulting mixture was stirred at room temperature for 4 hours.

Water was added to the reaction mixture, followed by extraction with a 1:2 mixture of toluene and ethyl acetate. The extract layer was washed with water and then a saturated aqueous sodium chloride solution, dried over anhydrous magnesium sulfate, and then distilled under reduced pressure to remove the solvent, whereby 1.47 g of ethyl 6-(2-tert-butoxy-2-oxoethoxy)-1-methyl-4-(trifluoromethyl)-1H-indole-2-carboxylate was obtained as a white solid.

Melting point: 98–100° C.

(b) Synthesis of [[2-(ethoxycarbonyl)-1-methyl-4-(trifluoromethyl)-1H-indol-6-yl]oxy]acetic Acid Under nitrogen, ethyl 6-(2-tert-butoxy-2-oxoethoxy)-1-methyl-4-(trifluoromethyl)-1H-indole-2-carboxylate (1.3 g, 3.24 mmol) was dissolved in acetic acid (20 ml), followed by adding thereto a 30% aqueous sulfuric acid solution (10 ml), and the resulting mixture was stirred at 50° C. for 1 hour. Crystals were precipitated and the reaction mixture became a white suspension. The reaction mixture was cooled to room temperature, followed by adding thereto water, and the crystals precipitated were collected by filtration, washed with water, and then dried under reduced pressure to obtain 1.17 g of [[2-(ethoxycarbonyl)-1-methyl-4-(trifluoromethyl)-1H-indol-6-yl]oxy]acetic acid as white crystals.

Melting point: 200–201.5° C.

(c) Synthesis of [[2-[[[amino(imino)methyl]amino]-carbonyl]-1-methyl-4-(trifluoromethyl)-1H-indol-6-yl]oxy]acetic Acid Under nitrogen, sodium methoxide (0.782 g, 14.48 mmol) was suspended in dimethylformamide (6 ml), followed by adding thereto guanidine hydrochloride (1.38 g, 14.48 mmol), and the resulting mixture was stirred at room temperature for 1 hour.

Separately, [[2-(ethoxycarbonyl)-1-methyl-4-(trifluoromethyl)-1H-indol-6-yl]oxy]acetic acid (0.50 g, 1.45 mmol) was dissolved in dimethylformamide (4 ml), and the resulting solution was added to the guanidine solution previously prepared. The reaction was carried out at room temperature for 22 hours.

Water was added to the reaction mixture to effect dissolution and the insoluble material was filtered off. The residue was adjusted to a pH of about 4 with a 1N aqueous hydrochloric acid solution and stirred at room temperature for 30 minutes. The white solid precipitated was collected by filtration, washed with water, and then dried under reduced pressure to obtain 0.471 g of [[2-[[amino(imino)-methyl]amino]carbonyl]-1-methyl-4-(trifluoromethyl)-1H-indol-6-yl]-oxy]acetic acid as a white solid.

Melting point: 250–266° C. (decomp.).

MS (ESI) (m/z): 359 (M+H$^+$).

The following compounds of Examples 22 to 26 were synthesized according to the process described in Example 21.

EXAMPLE 22

[[2-[[[Amino(imino)methyl]amino]carbonyl]-1-methyl-4-(trifluoromethyl)-1H-indol-7-yl]oxy]acetic Acid Melting point: 224–233° C. (decomp.).

EXAMPLE 23

[[2-[[[Amino(imino)methyl]amino]carbonyl]-4-chloro-1-methyl-1H-indol-6-yl]oxy]acetic Acid Melting point: 257–260° C. (decomp.).

EXAMPLE 24

[[2-[[[Amino(imino)methyl]amino]carbonyl]-4-chloro-1-methyl-1H-indol-7-yl]oxy]acetic Acid Melting point: 210–225° C. (decomp.).

EXAMPLE 25

[[2-[[[Amino(imino)methyl]amino]carbonyl]-1,4-dimethyl-1H-indol-6-yl]oxy]acetic Acid Melting point: 260–270° C. (decomp.).

EXAMPLE 26

[[2-[[[Amino(imino)methyl]amino]carbonyl]-1,4-dimethyl-1H-indol-7-yl]oxy]acetic Acid Melting point: 248–252° C. (decomp.).

EXAMPLE 27

Synthesis of 3-[2-[[[amino(imino)methyl]-amino]carbonyl]-4-chloro-1H-indol-1-yl]-1-propanesulfonic Acid (a) Synthesis of 3-[4-chloro-2-(methoxycarbonyl)-1H-indol-1-yl]-1-propanesulfonic Acid Under nitrogen, a suspension of 60% sodium hydride (0.178 g, 4.45 mmol) in tetrahydrofuran (5 ml) was cooled with ice, followed by adding dropwise thereto a solution of ethyl 4-chloro-1H-indole-2-carboxylate (0.838 g, 4.00 mmol) in tetrahydrofuran (5 ml), and the resulting mixture was stirred at room temperature for 1.5 hours. The mixture was re-cooled with ice, followed by adding dropwise thereto a solution of 1,3-propanesultone (0.540 g, 4.42 mmol) in tetrahydrofuran (2 ml), and the resulting mixture was stirred overnight at room temperature.

The solvent was distilled off from the reaction solution and water was added to the residue. The mixture thus obtained was washed twice with diethyl ether (a small amount of sodium chloride was added to the mixture because the mixture was hardly separated as it was). After the aqueous layer was adjusted to pH 1 to 2 with 4N hydrochloric acid, ethyl acetate was added and then sodium chloride was added until the aqueous layer was saturated therewith. Since an oil was separated as an intermediate layer, it was collected together with the organic layer. Extraction from the aqueous layer with ethyl acetate was carried out twice. The solvent was distilled off from the combined organic layer, and the remaining water was removed as an azeotrope with toluene to obtain 1.406 g of crude 3-[4-chloro-2-(methoxycarbonyl)-1H-indol-1-yl]-1-propanesulfonic acid.

Melting point: 183–248° C. (decomp.).

(b) Synthesis of 3-[2-[[[amino(imino)methyl]amino]-carbonyl]-4-chloro-1H-indol-1-yl]-1-propanesulfonic Acid Under nitrogen, guanidine hydrochloride (3.820 g, 40.0 mmol) was added to a suspension of sodium methoxide (2.165 g, 40.0 mmol) in DMF (20 ml) and stirred for 1 hour, and then a solution of crude 3-[4-chloro-2-(methoxycarbonyl)-1H-indol-1-yl]-1-propanesulfonic acid (1.381 g) in DMF (5 ml) was added thereto and stirred overnight.

Water was added to the reaction solution under ice-cooling and the resulting mixture was washed twice with chloroform. Then, chloroform was added thereto to form two layers and the pH was adjusted to 3 to 4 with 4N hydrochloric acid to precipitate crystals. After stirring for a while, the crystals were collected by filtration and suspended in methanol, and the resulting suspension was stirred for a while. The crystals were collected by filtration and dried to obtain 0.937 g of 3-[2-[[[amino(imino)methyl]-amino] carbonyl]-4-chloro-1H-indol-1-yl]-1-propanesulfonic acid.

Melting point: 281° C. (decomp.).

MS (FAB+) (m/z): 359 (M+H$^+$).

The following compounds of Examples 28 and 29 were synthesized according to the process described in Example 27.

EXAMPLE 28

3-[2-[[[Amino(imino)methyl]amino]carbonyl]-4-(trifluoromethyl)-1H-indol-1-yl]-1-propanesulfonic Acid Melting point: >300° C.

MS (ESI) (m/z): 393 (M+H$^+$).

EXAMPLE 29

3-[2-[[[Amino(imino)methyl]amino]carbonyl]-4-methyl-1H-indol-1-yl]-1-propanesulfonic Acid Melting point: 298° C. (decomp.).

MS (FAB+) (m/z): 339 (M+H$^+$).

EXAMPLE 30

Synthesis of 2-[2-[[[amino(imino)methyl]-amino] carbonyl]-1-methyl-4-(trifluoromethyl)-1H-indol-6-yl]oxy] ethanesulfonic Acid (a) Synthesis of 2-(2-bromoethoxy)tetrahydro-2H-pyran Under nitrogen, 2-bromoethanol (20 g, 160 mmol) and 3,4-dihydro-2H-pyran (26.9 g, 320 mmol) were dissolved in tetrahydrofuran (20 ml), followed by adding thereto p-toluenesulfonic acid (0.5 g), and the resulting mixture was stirred at room temperature for 2 hours.

Sodium acetate was added to the reaction mixture, and the mixture thus obtained was stirred at room temperature for 30 minutes and then filtered. The solvent was distilled off from the filtrate under reduced pressure to obtain a concentrated residue. The concentrated residue was purified by a silica gel column chromatography (eluent: n-hexane/ethyl acetate= 100/1) to obtain 15.9 g of 2-(2-bromoethoxy)tetrahydro-2H-pyran.

(b) Synthesis of Ethyl 1-methyl-6-[2-(tetrahydro-2H-pyran-2-yloxy)ethoxy]-4-(trifluoromethyl)-1H-indole-2-carboxylate Under nitrogen, 60% sodium hydride (86 mg, 2.15 mmol) was suspended in N,N-dimethylformamide (3 ml), followed by adding thereto a solution of ethyl 6-hydroxy-1-methyl-4-(trifluoromethyl)-1H-indole-2-carboxylate (501 mg, 1.74 mmol) in N,N-dimethylformamide (2 ml) and potassium iodide (34 mg, 0.21 mmol), and the resulting mixture was stirred at room temperature for 1 hour. Then, 2-(2-bromoethoxy)-tetrahydro-2H-pyran (334 mg, 2.14 mmol) was added dropwise thereto, and the resulting mixture was allowed to stand overnight at room temperature.

Water (40 ml) was added to the reaction mixture, followed by extraction with a 1:1 mixture of ethyl acetate and toluene. The extract layer was washed with a saturated aqueous sodium chloride solution, dried over anhydrous magnesium sulfate, filtered, and then distilled under reduced pressure to remove the solvent. The concentrated residue thus obtained was purified by a silica gel column chromatography (eluent: n-hexane/ethyl acetate=5/1) to obtain 298 mg of ethyl 1-methyl-6-[2-(tetrahydro-2H-pyran-2-yloxy)ethoxy]-4-(trifluoromethyl)-1H-indole-2-carboxylate.

(c) Synthesis of Ethyl 6-(2-hydroxyethoxy)-1-methyl-4-(trifluoromethyl)-1H-indole-2-carboxylate Under nitrogen, ethyl 1-methyl-6-[2-(tetrahydro-2H-pyran-2-yloxy)ethoxy]-4-(trifluoromethyl)-1H-indole-2-carboxylate (410 mg) was dissolved in THF (3 ml), followed by adding dropwise thereto a 1N aqueous hydrochloric acid solution (2 ml), and the resulting mixture was allowed to stand overnight at room temperature.

Water was added to the reaction mixture, followed by extraction with ethyl acetate. The extract layer was washed with a saturated aqueous sodium chloride solution, dried over anhydrous magnesium sulfate, filtered, and then distilled under reduced pressure to remove the solvent. The concentrated residue thus obtained was purified by a silica gel column chromatography (eluent: n-hexane/ethyl acetate=5/1 and 1/1) to obtain 264 mg of ethyl 6-(2-hydroxyethoxy)-1-methyl-4-(trifluoromethyl)-1H-indole-2-carboxylate.

(d) Synthesis of Ethyl 6-(2-iodoethoxy)-1-methyl-4-(trifluoromethyl)-1H-indole-2-carboxylate Under nitrogen, ethyl 6-(2-hydroxyethoxy)-1-methyl-4-(trifluoromethyl)-1H-indole-2-carboxylate (250 mg, 0.76 mmol) was dissolved in a mixture of toluene (2.5 ml) and acetonitrile (0.5 ml), and triphenylphosphine (259 mg, 0.99 mmol) and imidazole (131 mg, 1.9 mmol) were added thereto at room temperature. After the resulting mixture was cooled with ice, iodine (234 mg, 0.92 mmol) was added thereto and the mixture thus obtained was stirred under ice-cooling for 1.5 hours and then at room temperature for 2 hours.

Ice water was poured into the reaction mixture, followed by extraction with ethyl acetate. The extract layer was washed with an aqueous sodium thiosulfate solution and a saturated aqueous sodium chloride solution, dried over anhydrous magnesium sulfate, filtered, and then distilled under reduced pressure to remove the solvent. The concentrated residue thus obtained was purified by a silica gel column chromatography (eluent: n-hexane/ethyl acetate=5/

1) to obtain 318 mg of ethyl 6-(2-iodoethoxy)-1-methyl-4-(trifluoromethyl)-1H-indole-2-carboxylate.

(e) Synthesis of 2-[[2-(ethoxycarbonyl)-1-methyl-4-(trifluoromethyl)-1H-indol-6-yl]oxy]ethanesulfonic Acid Under nitrogen, ethyl 6-(2-iodoethoxy)-1-methyl-4-(trifluoromethyl)-1H-indole-2-carboxylate (300 mg, 0.68 mmol) was suspended in a mixture of ethanol and a solution of sodium sulfite (860 mg, 6.82 mmol) in water (6 ml), and the resulting suspension was stirred at 100° C. for 1 hour.

The reaction mixture was cooled to room temperature, adjusted to pH 1 by dropwise addition of a 6N aqueous hydrochloric acid solution, and then extracted with ethyl acetate. The extract layer was washed with a saturated aqueous sodium chloride solution adjusted to pH 1 with a 6N aqueous hydrochloric acid solution, and was dried over anhydrous magnesium sulfate, filtered, and then distilled under reduced pressure to remove the solvent. The concentrated residue thus obtained was purified by a silica gel column chromatography (eluent: acetic acid/methanol/chloroform=1/10/90) to obtain 120 mg of 2-[[2-(ethoxycarbonyl)-1-methyl-4-(trifluoromethyl)-1H-indol-6-yl]oxy]ethanesulfonic acid.

(f) Synthesis of 2-[2-[[[amino(imino)methyl]amino]carbonyl]-1-methyl-4-(trifluoromethyl)-1H-indol-6-yl]oxylethanesulfonic Acid Under nitrogen, sodium methoxide (138 mg, 2.53 mmol) was suspended in N,N-dimethylformamide (1 ml), followed by adding thereto guanidine hydrochloride (248 mg, 2.60 mmol), and the resulting mixture was stirred at room temperature for 1 hour. A solution of 2-[[2-(ethoxycarbonyl)-1-methyl-4-(trifluoromethyl)-1H-indol-6-yl]oxy]ethanesulfonic acid (101 mg, 0.26 mmol) in N,N-dimethylformamide (3 ml) was added thereto, and the resulting mixture was stirred overnight at room temperature.

A 6N aqueous hydrochloric acid solution was poured into the reaction mixture, followed by adding thereto a small volume of a saturated aqueous sodium chloride solution, and the solid formed was collected by filtration.

The solid collected by filtration was suspended in methanol, re-collected by filtration, washed with methanol, and then dried under reduced pressure to obtain 66 mg of 2-[[2-[[[amino(imino)-methyl]amino]carbonyl]-1-methyl-4-(trifluoromethyl)-1H-indol-6-yl]oxy]ethanesulfonic acid.

Melting point: 325° C. (decomp.).

ESI-MS (m/z): 409 (M$^+$+1).

The following compound of Example 31 was synthesized according to the process described in Example 30.

EXAMPLE 31

2-[[2-[[[Amino(imino)methyl]amino]carbonyl]-1-methyl-4-(trifluoromethyl)-1H-indol-7-yl]oxy]-ethanesulfonic Acid Melting point: 275° C. (decomp.).

EXAMPLE 32

Synthesis of 3-[[2-[[[amino(imino)methyl]-amino]carbonyl]-1-methyl-4-(trifluoromethyl)-1H-indol-6-yl]oxy[-1-propanesulfonic Acid (a) Synthesis of 3-[[2-(ethoxycarbonyl)-1-methyl-4-(trifluoromethyl)-1H-indol-6-yl]oxy]-1-propanesulfonic Acid Under nitrogen, a suspension of 60% sodium hydride (158 mg, 3.95 mmol) in tetrahydrofuran (1.5 ml) was cooled with ice, followed by adding thereto a solution of ethyl 6-hydroxy-1-methyl-4-(trifluoromethyl)-1H-indole-2-carboxylate (1.00 g, 3.48 mmol) in tetrahydrofuran (10 ml), and the resulting mixture was stirred at room temperature for about 1 hour until a transparent solution was obtained.

1,3-Propanesultone (485 mg, 3.97 mmol) was added dropwise to the obtained solution and the resulting mixture was stirred at room temperature for 8 hours. After the tetrahydrofuran was distilled off under reduced pressure, water was added to the concentrated residue thus obtained and the resulting mixture was washed with diethyl ether. Sodium chloride was added to the aqueous layer, and the solid precipitated was collected by filtration and re-dissolved in water. The resulting solution was adjusted to pH 1 with a 1N aqueous hydrochloric acid solution, and the solid precipitated was collected by filtration, washed with diethyl ether, and then dried under reduced pressure to obtain 1.12 g of 3-[[2-(ethoxycarbonyl)-1-methyl-4-(trifluoromethyl)-1H-indol-6-yl]oxy]-1-propanesulfonic acid.

(b) Synthesis of 3-[[2-[[[amino(imino)methyl]amino]-carbonyl]-1-methyl-4-(trifluoromethyl)-1H-indol-6-yl]oxy]-1-propanesulfonic Acid Under nitrogen, sodium methoxide (2.65 g, 49.00 mmol) was suspended in N,N-dimethylformamide (10 ml), followed by adding thereto guanidine hydrochloride (4.68 g, 48.99 mmol), and the resulting mixture was stirred at room temperature for 1 hour. Then, 3-[[2-(ethoxycarbonyl)-1-methyl-4-(trifluoromethyl)-1H-indol-6-yl]oxy]-1-propanesulfonic acid (1.00 g, 2.44 mmol) was added thereto, and the resulting mixture was stirred overnight at room temperature.

The reaction mixture was poured into ice water (200 ml), followed by adding thereto chloroform (50 ml), and the solid precipitated was collected by filtration. The solid collected by filtration was re-suspended in water, and the resulting suspension was adjusted to pH 1 with a 6N aqueous hydrochloric acid solution with stirring at room temperature, and then stirred. Thereafter, the solid was collected by filtration, washed with diethyl ether and methanol, and then dried under reduced pressure to obtain 716 mg of 3-[[2-[[[amino(imino)methyl]amino]carbonyl]-1-methyl-4-(trifluoromethyl)-1H-indol-6-yl]oxy]-1-propanesulfonic acid.

Melting point: 310° C. (decomp.).

FAB-MS (m/z): 423 (M$^+$+1).

The following compounds of Example 33 to 36 were synthesized according to the process described in Example 32.

EXAMPLE 33

3-[[2-[[[Amino(imino)methyl]amino]carbonyl]-1-methyl-4-(trifluoromethyl)-1H-indol-7-yl]oxy]-1-propanesulfonic Acid Melting point: 272–300° C. or higher (decomp.).

FAB-MS (m/z): 423 (M$^+$+1).

EXAMPLE 34

3-[[2-[[[Amino(imino)methyl]amino]carbonyl]-4-chloro-1-methyl-1H-indol-6-yl]oxy]-1-propanesulfonic Acid Melting point: 325° C. (decomp.).

FAB-MS (m/z): 389 (M$^+$+1).

EXAMPLE 35

3-[[2-[[[Amino(imino)methyl]amino]carbonyl]-1,4-dimethyl-1H-indol-6-yl]oxy]-1-propanesulfonic Acid Melting point: 290° C. (decomp.).

EXAMPLE 36

3-[[2-[[[Amino(imino)methyl]amino]carbonyl]-1,4-dimethyl-1H-indol-7-yl]oxy]-1-propanesulfonic Acid Melting point: 278–300° C. or higher (decomp.).

FAB-MS (m/z): 369 (M$^+$+1).

EXAMPLE 37

Synthesis of [2-[[[amino(imino)methyl]amino]-carbonyl]-1-methyl-4-(trifluoromethyl)-1H-indol-6-yl]-methanesulfonic Acid (a) Synthesis of [2-(ethoxycarbonyl)-1-methyl-4-(trifluoromethyl)-1H-indol-6-yl]methanesulfonic Acid Under nitrogen, ethyl 6-(bromomethyl)-1-methyl-4-(trifluoromethyl)-1H-indole-2-carboxylate (270 mg, 0.741 mmol) was suspended in ethanol (2 ml), followed by adding thereto a solution of sodium sulfite (187 mg, 1.48 mmol) in water (4 ml), and the resulting mixture was stirred at 100° C. for 1 hour.

After the mixture was cooled to room temperature, water (20 ml) was added thereto and the resulting mixture was adjusted to a pH of 1 or lower with a 6N aqueous hydrochloric acid solution and extracted with ethyl acetate. The extract layer was washed with a small volume of a saturated aqueous sodium chloride solution, dried over anhydrous magnesium sulfate, filtered, and then distilled under reduced pressure to remove the solvent, whereby a concentrated residue was obtained. The concentrated residue was purified by a silica gel column chromatography (eluent: chloroform/methanol=5/1 to 1/1) to obtain 224 mg of [2-(ethoxycarbonyl)-1-methyl-4-(trifluoromethyl)-1H-indol-6-yl]methanesulfonic acid as a white solid.

(b) Synthesis of [2-[[[amino(imino)methyl]amino]-carbonyl]-1-methyl-4-(trifluoromethyl)-1H-indol-6-yl]methanesulfonic Acid Under nitrogen, sodium methoxide (296 mg, 5.48 mmol) was suspended in N,N-dimethylformamide (3 ml), followed by adding thereto guanidine hydrochloride (523 mg, 5.48 mmol), and the resulting mixture was stirred at room temperature for 1 hour.

Separately, [2-(ethoxycarbonyl)-1-methyl-4-(trifluoromethyl)-1H-indol-6-yl]methanesulfonic acid (200 mg, 0.547 mmol) was suspended in N,N-dimethylformamide (2 ml), followed by adding thereto the guanidine solution previously prepared, and the resulting mixture was stirred at room temperature for 4.5 hours.

After water was added to the reaction mixture to effect dissolution, the resulting solution was adjusted to pH 1 with a 1N aqueous hydrochloric acid solution and stirred at room temperature for 15 minutes. The white solid precipitated was collected by filtration, washed with a 1N aqueous hydrochloric acid solution, and then suspended in methanol (4 ml). The white solid was re-collected by filtration, washed with methanol, and then dried under reduced pressure to obtain 160 mg of [2-[[[amino(imino)methyl]amino]-carbonyl]-1-methyl-4-(trifluoromethyl)-1H-indol-6-yl]methanesulfonic acid as a white solid.

Melting point: 300° C. or higher.

ESI-MS (m/z): 379 (M$^+$+1).

The following compound of Example 38 was synthesized according to the process described in Example 37.

EXAMPLE 38

[2-[[[Amino(imino)methyl]amino]carbonyl]-1-methyl-4-(trifluoromethyl)-1H-indol-7-yl]methanesulfonic Acid Melting point: 300° C. or higher.

EXAMPLE 39

Synthesis of 2-[2-[[[amino(imino)methyl]-amino]carbonyl]-1-methyl-4-(trifluoromethyl)-1H-indol-6-yl]ethanesulfonic Acid (a) Synthesis of Ethyl 6-(2-hydroxyethyl)-1-methyl-4-(trifluoromethyl)-1H-indole-2-carboxylate Under nitrogen, ethyl 1-methyl-4-(trifluoromethyl)-6-vinyl-1H-indole-2-carboxylate (1.0 g, 3.36 mmol) was dissolved in tetrahydrofuran (5 ml), and 9-borabicyclo[3,3,1] nonane (a 0.5 mol/liter tetrahydrofuran solution) (13.46 ml, 6.73 mmol) was added dropwise thereto under ice-cooling over a period of 30 minutes.

The resulting mixture was stirred at room temperature for 5.5 hours, followed by adding thereto water (1 ml) and a 2N aqueous sodium hydroxide solution (5 ml), and a 31% aqueous hydrogen peroxide solution (5 ml) was added dropwise thereto over a period of 15 minutes.

The reaction mixture was stirred for 7 hours, adjusted to pH 2 with a 1N aqueous hydrochloric acid solution, and then extracted twice with ethyl acetate. The combined extract layer was washed twice with water and then once with a saturated aqueous sodium chloride solution, dried over anhydrous magnesium sulfate, filtered, and then distilled under reduced pressure to remove the solvent, whereby a concentrated residue was obtained. The concentrated residue was purified by a silica gel column chromatography (eluents: n-hexane/ethyl acetate=10/1 to 0/10 and 1% acetic acid/ethyl acetate) to obtain 0.660 g of ethyl 6-(2-hydroxyethyl)-1-methyl-4-(trifluoromethyl)-1H-indole-2-carboxylate as a white solid.

(b) Synthesis of Ethyl 6-(2-iodoethyl)-1-methyl-4-(trifluoromethyl-1H-indole-2-carboxylate Under nitrogen, ethyl 6-(2-hydroxyethyl)-1-methyl-4-(trifluoromethyl)-1H-indole-2-carboxylate (600 mg, 1.90 mmol) was dissolved in a mixture of toluene (30 ml) and acetonitrile (4 ml), and then imidazole (324 mg, 4.76 mmol) and triphenylphosphine (649 mg, 2.74 mmol) were substantially dissolved therein. Iodine (580 mg, 2.28 mmol) was added thereto under ice-cooling and the resulting mixture was stirred at room temperature for 1 hour.

An aqueous sodium thiosulfate solution was added to the reaction mixture, and the mixture thus obtained was stirred for 10 minutes and then separated. The organic layer was washed twice with water and then once with a saturated aqueous sodium chloride solution, dried over anhydrous magnesium sulfate, filtered, and then distilled under reduced pressure to remove the solvent, whereby a concentrated residue was obtained. The concentrated residue was purified by a silica gel column chromatography (eluent: n-hexane/ethyl acetate=50/1, 30/1 and 20/1) to obtain 717 mg of ethyl 6-(2-iodoethyl)-1-methyl-4-(trifluoromethyl)-1H-indole-2-carboxylate as a white solid.

(c) Synthesis of 2-[2-(ethoxycarbonyl)-1-methyl-4-(trifluoromethyl)-1H-indol-6-yl]ethanesulfonic Acid Under nitrogen, ethyl 6-(2-iodoethyl)-1-methyl-4-(trifluoromethyl)-1H-indole-2-carboxylate (350 mg, 0.823 mmol) and sodium sulfite (1.04 g, 8.23 mmol) were suspended in a mixture of water (5 ml) and ethanol (2 ml), and the resulting suspension was stirred at 100° C. for 5.5 hours (sodium sulfite (0.519 g), water (3 ml) and ethanol (4 ml) were added during the stirring).

The reaction mixture was cooled to room temperature, adjusted to pH 1 with a 1N aqueous hydrochloric acid solution, and then extracted twice with ethyl acetate. The combined extract layer was washed with a mixture of a saturated aqueous sodium chloride solution and a 1N aqueous hydrochloric acid solution, dried over anhydrous magnesium sulfate, and then distilled under reduced pressure to remove the solvent, whereby a concentrated residue was obtained. The concentrated residue was purified by a silica gel column chromatography (eluent: chloroform/methanol=5/1 to 1/1) to obtain 0.246 g of 2-[2-(ethoxycarbonyl)-1-methyl-4-(trifluoromethyl)-1H-indol-6-yl]-ethanesulfonic acid as a white solid.

(d) Synthesis of 2-[2-[[[amino(imino)methyl]amino]-carbonyl]-1-methyl-4-(trifluoromethyl)-1H-indol-6-yl] ethanesulfonic Acid Under nitrogen, sodium methoxide (285 mg, 5.27 mmol) was suspended in N,N-dimethylformamide (5 ml), followed by adding thereto guanidine hydrochloride (504 mg, 5.27 mmol), and the resulting mixture was stirred at room temperature for 1 hour.

Separately, 2-[2-(ethoxycarbonyl)-1-methyl-4-(trifluoromethyl)-1H-indol-6-yl]ethanesulfonic acid (200 mg, 0.527 mmol) was dissolved (suspended) in N,N-dimethylformamide (2 ml), followed by adding thereto the guanidine solution previously prepared, and the resulting mixture was stirred at room temperature for 7 hours.

After water was added to the reaction mixture to effect dissolution, the resulting solution was adjusted to pH 1 with a 1N aqueous hydrochloric acid solution and stirred at room temperature for 15 minutes. The white solid precipitated was collected by filtration, washed with a 1N aqueous hydrochloric acid solution, and then suspended in methanol (4 ml). The white solid was re-collected by filtration, washed with methanol, and then dried under reduced pressure to obtain 148 mg of 2-[2-[[[amino(imino)methyl]amino]-carbonyl]-1-methyl-4-(trifluoromethyl)-1H-indol-6-yl] ethanesulfonic acid as a white solid.

Melting point: 300° C. or higher.

ESI-MS (m/z): 393 ($M^+$+1).

The following compounds of Examples 40 to 42 were synthesized according to the process described in Example 39.

EXAMPLE 40

2-[2-[[[Amino(imino)methyl]amino]carbonyl]-1-methyl-4-(trifluoromethyl)-1H-indol-7-yl]ethanesulfonic Acid Melting point: 300° C. or higher.

FAB-MS (m/z): 393 ($M^+$+1).

EXAMPLE 41

2-[2-[[[Amino(imino)methyl]amino]carbonyl]-4-chloro-1-methyl-1H-indol-6-yl]ethanesulfonic Acid Melting point: 300° C. or higher.

ESI-MS (m/z): 359 ($M^+$+1).

EXAMPLE 42

2-[2-[[[Amino(imino)methyl]amino]carbonyl]-1,4-dimethyl-1H-indol-6-yl]ethanesulfonic Acid Melting point: 300° C. or higher (decomp.).

ESI-MS (m/z): 339 ($M^+$+1).

EXAMPLE 43

Synthesis of 2-[[[amino(imino)methyl]amino]-carbonyl]-1-methyl-4-(trifluoromethyl)-1H-indol-6-ylphosphonic Acid (a) Synthesis of Ethyl 6-(diethoxyphosphoryl)-1-methyl-4-(trifluoromethyl)-1H-indole-2-carboxylate Under nitrogen, ethyl 1-methyl-4-(trifluoromethyl)-6-[[(trifluoromethyl)sulfonyl]oxy]-1H-indole-2-carboxylate (2.0 g, 4.77 mmol) was dissolved in triethylamine (20 ml), followed by adding thereto diethyl phosphite (0.74 ml, 5.72 mmol) and tetrakis(triphenylphosphine)palladium(0) (276 mg, 0.238 mmol), and the resulting mixture was sealed up in an autoclave and stirred for 6 hours while maintaining the mixture at 120° C.

The solvent was distilled off under reduced pressure and the resulting concentrated residue was purified by a silica gel column chromatography (eluents: n-hexane/ethyl acetate=4/1, 2/1 and 1/1) to obtain 1.61 g of ethyl 6-(diethoxyphosphoryl)-1-methyl-4-(trifluoromethyl)-1H-indole-2-carboxylate.

(b) Synthesis of Diethyl 2-[[[amino(imino)methyl]-amino] carbonyl]-1-methyl-4-(trifluoromethyl)-1H-indol-6-ylphosphonate Under nitrogen, sodium methoxide (1.99 g, 36.83 mmol) was suspended in N,N-dimethylformamide (30 ml), followed by adding thereto guanidine hydrochloride (3.52 g, 36.83 mmol), and the resulting mixture was stirred at room temperature for 1 hour.

A solution of ethyl 6-(diethoxyphosphoryl)-1-methyl-4-(trifluoromethyl)-1H-indole-2-carboxylate (1.50 g, 3.68 mmol) in N,N-dimethylformamide (15 ml) was added to the reaction mixture, followed by stirring at room temperature for 1 hour.

Water (about 200 ml) was added to the reaction mixture and the resulting mixture was stirred to adjust the pH to 10, and was extracted twice with a 1:2 mixture of toluene and ethyl acetate. The combined extract layer was washed twice with water and then once with a saturated aqueous sodium chloride solution, dried over anhydrous magnesium sulfate, and then distilled under reduced pressure to remove the solvent, whereby a concentrated residue was obtained. The concentrated residue was purified by a silica gel column chromatography (eluent: chloroform/methanol=95/5) to obtain 1.01 g of diethyl 2-[[[amino(imino)-methyl]amino] carbonyl]-1-methyl-4-(trifluoromethyl)-1H-indol-6-ylphosphonate as a white solid.

(c) Synthesis of 2-[[[amino(imino)methyl]-amino] carbonyl]-1-methyl-4-(trifluoromethyl)-1H-indol-6-ylphosphonic Acid Methanesulfonate Under nitrogen, diethyl 2-[[[amino(imino)-methyl] amino]carbonyl]-1-methyl-4-(trifluoromethyl)-1H-indol-6-ylphosphonate (200 mg, 0.476 mmol) was dissolved in dichloromethane (2 ml), and bromotrimethylsilane (0.220 ml, 1.67 mmol) was added thereto.

The resulting mixture was stirred at room temperature for 17 hours, concentrated to dryness under reduced pressure, dissolved in a mixture of dichloromethane (3 ml) and methanol (1 ml), and then re-concentrated to dryness under reduced pressure to obtain a concentrated residue (white and amorphous).

The concentrated residue was suspended in isopropyl alcohol (5 ml), followed by adding thereto methanesulfonic acid (46 µl, 0.714 mmol), and the resulting mixture was stirred at room temperature. (The mixture became a transparent solution and then white crystals were re-precipitated).

After the re-precipitation of the crystals, the mixture was stirred for 30 minutes and the crystals were collected by filtration, washed with a small volume of isopropyl alcohol, and then dried under reduced pressure to obtain 146 mg of 2-[[[amino(imino)methyl]amino]carbonyl]-1-methyl-4-(trifluoromethyl)-1H-indol-6-ylphosphonic acid methanesulfonate as white crystals.

Melting point: 286° C. (decomp.).

ESI-MS (m/z): 365 ($M^+$+1).

The following compound of Example 44 was synthesized according to the process described in Example 43.

EXAMPLE 44

2-[[[Amino(imino)methyl]amino]carbonyl]-1-methyl-4-(trifluoromethyl)-1H-indol-7-ylphosphonic Acid Methanesulfonate Melting point: 258° C. (decomp.).

EXAMPLE 45

Synthesis of [[2-[[[amino(imino)methyl]-amino]carbonyl]-1-methyl-4-(trifluoromethyl)-1H-indol-6-yl]oxy]-methylphosphonic Acid (a) Synthesis of (diethoxyphosphoryl)methyl Trifluoromethanesulfonate Under nitrogen, diethylhydroxymethyl phosphonate (3.0 g, 17.84 mmol) was dissolved in a mixture of dichloromethane (30 ml) and triethylamine (4.97 ml, 35.69 mmol), and the solution was cooled with salt and ice. Trifluoromethanesulfonic acid anhydride (3.30 ml, 19.63 mmol) was added dropwise thereto over a period 20 minutes, and the resulting mixture was stirred for 2 hours while maintaining the temperature.

Water was added to the reaction mixture and the resulting mixture was warmed to room temperature and extracted with chloroform. The organic layer was washed with water and then a saturated aqueous sodium chloride solution, dried over anhydrous magnesium sulfate, and then distilled under reduced pressure to remove the solvent, whereby 4.64 g of (diethoxyphosphoryl)methyl trifluoromethanesulfonate was obtained as a dark-brown oil.

(b) Synthesis of Ethyl 6-[(diethoxyphosphoryl)-methoxy]-1-methyl-4-(trifluoromethyl)-1H-indole-2-carboxylate Under nitrogen, 60% sodium hydride (0.146 g, 3.66 mmol) was suspended in N,N-dimethylformamide (1 ml), followed by adding dropwise thereto a solution of ethyl 6-hydroxy-1-methyl-4-(trifluoromethyl)-1H-indole-2-carboxylate (1.0 g, 3.48 mmol) in N,N-dimethylformamide (9 ml), and the resulting mixture was stirred at room temperature for 30 minutes.

The reaction mixture was cooled with ice, followed by adding dropwise thereto a solution of (diethoxyphosphoryl)methyl trifluoromethanesulfonate (1.57 g, 5.22 mmol) in N,N-dimethylformamide (5 ml), and the resulting mixture was stirred under ice-cooling for 3 hours and then at room temperature for 20 hours.

A 1N aqueous hydrochloric acid solution was added to the reaction mixture and stirred to adjust the pH to 1, followed by extraction with a 1:1 mixture of toluene and ethyl acetate (twice). The combined extract layer was washed with water and then a saturated aqueous sodium chloride solution, dried over anhydrous magnesium sulfate, and then distilled under reduced pressure to remove the solvent, whereby a concentrated residue was obtained. The concentrated residue was purified by a silica gel column chromatography (eluent: n-hexane/ethyl acetate=3/1, 1/2 and 1/4) to obtain 1.15 g of ethyl 6-[(diethoxyphosphoryl)methoxy]1-methyl-4-(trifluoromethyl)-1H-indole-2-carboxylate as a white solid.

(c) Synthesis of Diethyl [[2-[[[amino(imino)methyl]-amino]carbonyl]-1-methyl-4-(trifluoromethyl)-1H-indol-6-yl]-oxy]methylphosphonate Under nitrogen, sodium methoxide (1.56 g, 22.87 mmol) was suspended in N,N-dimethylformamide (20 ml), followed by adding thereto guanidine hydrochloride (2.18 g, 22.90 mmol), and the resulting mixture was stirred at room temperature for 1 hour.

A solution of ethyl 6-[(diethoxyphosphoryl)methoxy]-1-methyl-4-(trifluoromethyl)-1H-indole-2-carboxylate (1.0 g, 2.29 mmol) in N,N-dimethylformamide (10 ml) was added to the reaction mixture, followed by stirring at room temperature for 5 hours.

Water was added to the reaction mixture to adjust the pH to 10, followed by extraction with a 1:1 mixture of toluene and ethyl acetate (twice). The combined extract layer was washed with water and then a saturated aqueous sodium chloride solution, dried over anhydrous magnesium sulfate, filtered, and then distilled under reduced pressure to remove the solvent. To the concentrated residue thus obtained were added chloroform (5 ml) and diethyl ether to effect crystallization, and the white crystals precipitated were collected by filtration, washed with diethyl ether, and then dried under reduced pressure to obtain 0.656 g of diethyl [[2-[[[amino(imino)methyl]amino]carbonyl]-1-methyl-4-(trifluoromethyl)-1H-indol-6-yl]oxy]-methylphosphonate as white crystals.

(d) Synthesis of [[2-[[[amino(imino)methyl]-amino]carbonyl]-1-methyl-4-(trifluoromethyl)-1H-indol-6-yl]oxy]methylphosphonic Acid Hydrobromide Under nitrogen, diethyl [[2-[[[amino(imino)-methyl]amino]carbonyl]-1-methyl-4-(trifluoromethyl)-1H-indol-6-yl]oxy]methylphosphonate (600 mg, 1.33 mmol) was suspended in dichloromethane (6 ml), and bromotrimethylsilane (0.62 ml, 4.66 mmol) was added thereto.

The resulting mixture was allowed to stand at room temperature for 25 hours (the disappearance of the starting material and intermediates was confirmed by HPLC) and then concentrated to dryness under reduced pressure. The concentrate was dissolved in a mixture of dichloromethane (9 ml) and methanol (3 ml), and the resulting solution was re-concentrated to dryness under reduced pressure. The concentrated residue thus obtained as a white solid was sufficiently suspended in isopropyl alcohol (4 ml), followed by adding thereto diethyl ether, and the crystals were collected by filtration, washed with diethyl ether, and then dried under reduced pressure to obtain 618 mg of [[2-[[[amino(imino)methyl]amino]carbonyl]-1-methyl-4-(trifluoromethyl)-1H-indol-6-yl]oxy]methylphosphonic acid hydrobromide as a white solid.

(e) Synthesis of [[2-[[[amino(imino)methyl]amino]-carbonyl]-1-methyl-4-(trifluoromethyl)-1H-indol-6-yl]oxy]methylphosphonic Acid

[[2-[[[Amino(imino)methyl]amino]carbonyl]-1-methyl-4-(trifluoromethyl)-1H-indol-6-yl]oxy]-methylphosphonic acid hydrobromide (617 mg, 1.30 mmol) was suspended in distilled water (20 ml) to adjust the pH to 1, and a 1.0N aqueous sodium hydroxide solution (3.90 g, 3.90 mmol) was added thereto to effect dissolution and adjust the pH to 11. The resulting solution was filtered and the filtrate was adjusted to pH 6 by addition of a 1.0N aqueous hydrochloric acid solution (2.60 ml, 2.60 mmol).

The filtrate was adjusted to pH 1 by further addition of a 1.0N aqueous hydrochloric acid solution (0.50 ml) and then adjusted to pH 6 by addition of a 1.0N aqueous sodium hydroxide solution (0.50 ml). The filtrate thus adjusted was stirred at room temperature for 15 minutes, and the white solid precipitated was collected by filtration, washed with water, and then dried under reduced pressure to obtain 525 mg of [[2-[[[amino(imino)methyl]amino]carbonyl]-1-methyl-4-(trifluoromethyl)-1H-indol-6-yl]oxy]methylphosphonic acid as a white solid.

Melting point: 292° C. (decomp.).

ESI-MS (m/z): 395 ($M^+$+1).

The following compounds of Examples 46 to 50 were synthesized according to the process described in Example 45.

EXAMPLE 46

[[2-[[[Amino(imino)methyl]amino]carbonyl]-1-methyl-4-(trifluoromethyl)-1H-indol-7-yl]oxy]methylphosphonic Acid Melting point: 260° C. (decomp.).
ESI-MS (m/z): 395 ($M^+$+1).

EXAMPLE 47

[[2-[[[Amino(imino)methyl]amino]carbonyl]-4-chloro-1-methyl-1H-indol-6-yl]oxy]methylphosphonic Acid Melting point: 263° C. (decomp.).
ESI-MS (m/z): 361 ($M^+$+1).

EXAMPLE 48

[[2-[[[Amino(imino)methyl]amino]carbonyl]-4-chloro-1-methyl-1H-indol-7-yl]oxy]methylphosphonic Acid Melting point: 247° C.
ESI-MS (m/z): 361 ($M^+$+1).

EXAMPLE 49

[[2-[[[Amino(imino)methyl]amino]carbonyl]-1,4-dimethyl-1H-indol-6-yl]oxy]methylphosphonic Acid Melting point: 300° C. or higher.
ESI-MS (m/z): 341 ($M^+$+1).

EXAMPLE 50

[[2-[[[Amino(imino)methyl]amino]carbonyl]-1,4-dimethyl-1H-indol-7-yl]oxy]methylphosphonic Acid Melting point: 270° C. (decomp.).
ESI-MS (m/z): 341 ($M^+$+1).

EXAMPLE 51

Synthesis of 2-[2-[[[amino(imino)methyl]-amino]carbonyl]-1-methyl-4-(trifluoromethyl)-1H-indol-6-yl]ethylphosphonic Acid (a) Synthesis of Ethyl 6-12-(diethoxyphosphoryl)-ethyl]-1-methyl-4-(trifluoromethyl)-1H-indole-2-carboxylate Under nitrogen, triethyl phosphite (605 µl, 3.53 mmol) was added to ethyl 6-(2-iodoethyl)-1-methyl-4-(trifluoromethyl)-1H-indole-2-carboxylate (300 mg, 0.706 mmol), and the resulting mixture was stirred for 1 hour on an oil bath at 140° C. while maintaining the temperature.

The excess triethyl phosphite was distilled off under reduced pressure as much as possible, and the resulting concentrated residue was purified by a silica gel column chromatography (eluent: n-hexane/ethyl acetate=15/1 to 0/10) to obtain 303 mg of ethyl 6-[2-(diethoxyphosphoryl)ethyl]-1-methyl-4-(trifluoromethyl)-1H-indole-2-carboxylate as a white solid.

(b) Synthesis of Diethyl 2-[2-[[[amino(imino)methyl]-amino]carbonyl]-1-methyl-4-(trifluoromethyl)-1H-indol-6-yl]ethylphosphonate Under nitrogen, sodium methoxide (335 mg, 6.20 mmol) was suspended in N,N-dimethylformamide (5 ml), followed by adding thereto guanidine hydrochloride (592 mg, 6.20 mmol), and the resulting mixture was stirred at room temperature for 1 hour.

A solution of ethyl 6-[2-(diethoxyphosphoryl)ethyl]-1-methyl-4-(trifluoromethyl)-1H-indole-2-carboxylate (270 mg, 0.620 mmol) in N,N-dimethylformamide (3 ml) was added to the reaction mixture, followed by stirring at room temperature for 5.5 hours.

The reaction mixture was adjusted to pH 10 by addition of water and extracted twice with a 1:3 mixture of toluene and ethyl acetate. The combined extract layer was washed twice with water and then once with a saturated aqueous sodium chloride solution, dried over anhydrous magnesium sulfate, filtered, and then distilled under reduced pressure to remove the solvent. To the concentrated residue thus obtained as a white solid were added chloroform (2 ml) and diethyl ether (10 ml) to effect crystallization. The white crystals precipitated were collected by filtration, washed with diethyl ether, and then dried under reduced pressure to obtain 226 mg of diethyl 2-[2-[[[amino(imino)methyl]amino]carbonyl]-1-methyl-4-(trifluoromethyl)-1H-indol-6-yl]ethylphosphonate as a white solid.

(c) Synthesis of 2-[2-[[[amino(imino)methyl]amino]-carbonyl]-1-methyl-4-(trifluoromethyl)-1H-indol-6-yl]ethylphosphonic Acid Hydrobromide Under nitrogen, diethyl 2-[2-[[[amino(imino)-methyl]amino]carbonyl]-1-methyl-4-(trifluoromethyl)-1H-indol-6-yl]ethylphosphonate (200 mg, 0.446 mmol) was dissolved in dichloromethane (2 ml), and bromotrimethylsilane (206 µl, 1.56 mmol) was added thereto.

After the resulting mixture was stirred at room temperature for 3 days (two 206-µl portions of bromotrimethylsilane were added during the stirring), the mixture was concentrated to dryness under reduced pressure. The concentrate was suspended in a mixture of dichloromethane (6 ml) and methanol (2 ml), and the suspension was concentrated to dryness under reduced pressure. The concentrated residue thus obtained as a white solid was sufficiently suspended in isopropyl alcohol (2 ml), followed by adding thereto diethyl ether (10 ml), and the crystals were collected by filtration, washed with diethyl ether, and then dried under reduced pressure to obtain 186 mg of 2-[2-[[[amino(imino)methyl]amino]carbonyl]-1-methyl-4-(trifluoromethyl)-1H-indol-6-yl]-ethylphosphonic acid hydrobromide as a white solid.

Melting point: 300° C. or higher.
ESI-MS (m/z): 393 ($M^+$+1).

(d) Synthesis of 2-[2-[[[amino(imino)methyl]amino]-carbonyl]-1-methyl-4-(trifluoromethyl)-1H-indol-6-yl]ethylphosphonic Acid 2-[2-[[[Amino(imino)methyl]amino]carbonyl]-1-methyl-4-(trifluoromethyl)-1H-indol-6-yl]ethylphosphonic acid hydrobromide (2.34 g, 4.24 mmol) was suspended in distilled water (100 ml), followed by adding thereto a 1.0N aqueous sodium hydroxide solution (12.7 ml, 12.7 mmol) to effect dissolution and adjust the pH to 11. The resulting solution was filtered and the filtrate was adjusted to a pH of 1 or lower with a 1.0N aqueous hydrochloric acid solution (8.48 ml, 8.48 mmol). After confirming that the filtrate became a white suspension, the filtrate was adjusted to pH 5 with a 1.0N aqueous sodium hydroxide solution and the white solid precipitated was collected by filtration. The white solid obtained was washed with water and then dried under reduced pressure to obtain 1.60 g of 2-[2-[[[amino(imino)methyl]amino]carbonyl]-1-methyl-4-(trifluoromethyl)-1H-indol-6-yl]-ethylphosphonic acid as a white solid.

Melting point: 277° C. (decomp.).
ESI-MS (m/z): 393 ($M^+$+1).

The following compounds of Examples 52 to 54 were synthesized according to the process described in Example 51.

EXAMPLE 52

2-[2-[[[Amino(imino)methyl]amino]carbonyl]-1-methyl-4-(trifluoromethyl)-1H-indol-7-yl]ethylphosphonic Acid Hydrobromide Melting point: 234° C. (decomp.).

ESI-MS (m/z): 393 ($M^+$+1).

EXAMPLE 53

2-[2-[[[Amino(imino)methyl]amino]carbonyl]-4-chloro-1-methyl-1H-indol-7-yl]ethylphosphonic Acid Melting point: 256° C. (decomp.).

ESI-MS (m/z): 359 ($M^+$+1).

EXAMPLE 54

2-[2-[[[Amino(imino)methyl]amino]carbonyl]-1,4-dimethyl-1H-indol-6-yl]ethylphosphonic Acid Melting point: 255° C. (decomp.).

ESI-MS (m/z): 339 ($M^+$+1).

EXAMPLE 55

Synthesis of 2-[[[amino(imino)methyl]amino]-carbonyl]-11-methyl-8-oxo-5,6,7,8-tetrahydro-4H-azocino[3,2,1-hi]indol-9-yl=hydrogen=sulfate Ethyl 5,6,7,8-tetrahydro-11-methyl-9-hydroxy-8-oxo-4H-azocino[3,2,1-hi]indole-2-carboxylate was synthesized from ethyl 6-benzyloxy-4-methyl-1H-indole-2-carboxylate by the process disclosed in the specification of U.S. Pat. No. 5,977,100, and then 2-[[[amino(imino)methyl]amino]carbonyl]-11-methyl-8-oxo-5,6,7,8-tetrahydro-4H-azocino[3,2,1-hi]indol-9-yl=hydrogen=sulfate was synthesized according to the process described in Example 1.

Melting point: 278° C. (decomp.).

EXAMPLE 56

Synthesis of 2-r[[amino(imino)methyl]amino]-carbonyl]-1-methyl-4-trifluoromethyl-1H-indol-7-yl Hydrogen Sulfate Monohydrate 2-[[[Amino(imino)methyl]amino]carbonyl]-1-methyl-4-trifluoromethyl-1H-indol-7-yl=hydrogen=sulfate (63.0 g, 0.166 mol) was suspended in a mixture of isopropyl alcohol (1,530 ml) and distilled water (1,365 ml) to adjust the pH to 4, and a 1.0N aqueous sodium hydroxide solution (165 ml, 0.165 mol) was added thereto with stirring at room temperature to effect dissolution and adjust the pH to 12. After activated carbon (6.4 g) was added thereto and stirred for 5 minutes, the resulting mixture was filtered and the activated carbon on a filter was washed with a 1:1 mixture of isopropyl alcohol and water (100 ml).

A 1.0N aqueous hydrochloric acid solution was added dropwise to the washings (pH 12) to adjust the pH to 5.4, followed by stirring at room temperature for 1 hour.

The light-yellow crystals precipitated were collected by filtration, washed twice with water (50 ml) and then twice with isopropyl alcohol (50 ml), and dried under reduced pressure to obtain 56.3 g of 2-[[[amino(imino)methyl]amino]carbonyl]-1-methyl-4-trifluoromethyl-1H-indol-7-yl=hydrogen=sulfate monohydrate as light-yellow crystals.

Melting point: 293° C. (decomp.).

ESI-MS (m/z): 381 ($M^+$+1).

| Elemental analysis (for $C_{12}H_{11}F_3N_4O_5S \cdot H_2O$) | | | |
|---|---|---|---|
| | C | H | N |
| Calculated (%) | 36.18 | 3.29 | 14.07 |
| Found (%) | 36.20 | 3.43 | 13.94 |

EXAMPLE 57

Synthesis of 3-[2-[[[amino(imino)methyl]-amino]carbonyl]-4-chloro-1H-indol-1-yl]-1-propanesulfonic Acid Monohydrate 3-[2-[[[amino(imino)methyl]amino]carbonyl]-4-chloro-1H-indol-1-yl]-1-propanesulfonic acid (56.0 g, 0.149 mol) was suspended in a mixture of tetrahydrofuran (2,240 ml) and distilled water (560 ml), followed by adding thereto triethylamine (22.53 g, 0.223 mol) to effect dissolution and adjust the pH to 12, and the resulting solution was filtered. A 2N aqueous hydrochloric acid solution was added dropwise to the filtrate to adjust the pH to 5.1, and distilled water (1,600 ml) was added dropwise thereto, followed by stirring at room temperature for 1 hour.

The white crystals precipitated were collected by filtration, washed successively with water, tetrahydrofuran and isopropyl alcohol, and then dried under reduced pressure to obtain 56.3 g of 3-[2-[[[amino(imino)methyl]amino]carbonyl]-4-chloro-1H-indol-1-yl]-1-propanesulfonic acid monohydrate as light-yellow crystals.

Melting point: 341° C. (decomp.).

| Elemental analysis (for $C_{12}H_{15}ClN_4O_4S \cdot H_2O$) | | | | |
|---|---|---|---|---|
| | C | H | N | Cl |
| Calculated (%) | 41.44 | 4.55 | 14.87 | 9.41 |
| Found (%) | 41.32 | 4.65 | 14.77 | 9.53 |

Test Example

Inhibitory Effect on the $Na^+/H^+$ Exchange Transport System (in vitro)

Test Method

A test was carried out according to the method of Iemori et al. (J. Hypertension, 8, 153(1990)). In detail, inhibitory effect on the $Na^+/H^+$ exchange transport system was evaluated by using as an indication a pH change in isolated ventricular myocytes (rat) under an acidic load.

Test Results

The results are shown in the following table.

| Example | Inhibitory effect on $Na^+/H^+$ exchange transport system $IC_{50}$ ($\mu M$) |
|---|---|
| 1 | 10 |
| 2 | 0.07 |
| 4 | 0.2 |

INDUSTRIAL APPLICABILITY

The present inventive compounds inhibit the sodium/proton ($Na^+/H^+$) exchange transport system and hence are useful as a therapeutic or prophylactic agent for diseases caused by the acceleration of the sodium/proton (Na+/H+) exchange transport system, for example, hypertension, arrhythmia, angina pectoris, cardiac insufficiency, cardiac hypertrophy, diabetes mellitus, organ disorders associated with ischemia or ischemic reperfusion [e.g. cardiac ischemic reperfusion-injury, acute renal failure, or disorder induced by surgical treatment such as organ transplantation or percutaneous transluminal coronary angioplasty (PTCA)], diseases caused by hyperplasia such as hyperplasia of fibroblast, hyperplasia of smooth muscle cells or hyperplasia of mesangium cells, which diseases are, for example, atherosclerosis, pulmonary fibrosis, hepatic fibrosis, renal fibrosis, glomerular nephrosclerosis, organ hypertrophy, prostatic hypertrophy, diabetic complications or restenosis after PTCA, or diseases caused by endotherial cell injury. Furthermore, the present inventive compounds exhibit only greatly lessened side effects on the nervous system, in particular, the central nervous system.

What is claimed is:

1. A compound represented by the formula (1):

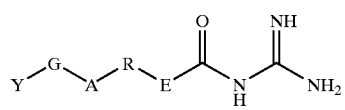

(1)

wherein E is a single bond; R is a substituted or unsubstituted indole; wherein the group represented by —C(O)NHC(NH)NH$_2$ in the formula (1) is attached to 2-position thereof;

A is a single bond or a substituted or unsubstituted lower alkylene group (one or more of the —CH$_2$— groups of said lower alkylene group may be replaced by one or more groups, which may be the same or different and are selected from the group consisting of a group represented by the formula: —O—, —S—, —N(R$^1$)— or —C(=O)—, a benzene ring and a cycloalkane ring (one or more of the —CH$_2$— groups in said cycloalkane ring may be replaced by one or more groups, which may be the same or different and are represented by the formula: —O—, —S—, —N(R$^2$)— or —C(=O)—) and any two adjacent atoms of said lower alkylene group may form a double bond or a triple bond);

G is a single bond or a group represented by the formula: —O— or —N(R$^{11}$)—;

Y is a group represented by the formula: —SO$_3$H, or —PO$_3$H$_2$, provided that G is a single bond when Y is a group represented by the formula: —PO$_3$H$_2$;

R$^1$, R$^{11}$ and R$^2$ are independently a hydrogen atom, a substituted or unsubstituted alkyl group, a substituted or unsubstituted alkenyl group, a substituted or unsubstituted alkynyl group, a substituted or unsubstituted cycloalkyl group, a substituted or unsubstituted cycloalkenyl group, a substituted or unsubstituted phenyl group, a substituted or unsubstituted naphthyl group, a substituted or unsubstituted heterocyclic group, or a substituted or unsubstituted acyl group;

or a prodrug of said compound, or a pharmaceutically acceptable salt of said compound or prodrug.

2. A compound, a prodrug thereof or a pharmaceutically acceptable salt of the compound or prodrug according to claim 1, wherein A is a single bond, and G is a group represented by the formula: —O—.

3. A compound, a prodrug thereof or a pharmaceutically acceptable salt of the compound or prodrug according to claim 1, wherein Y is a group represented by the formula: —SO$_3$H.

4. A compound, a prodrug thereof or a pharmaceutically acceptable salt of the compound or prodrug according to claim 1, wherein Y is a group represented by the formula: —PO$_3$H$_2$.

5. A compound, a prodrug thereof or a pharmaceutically acceptable salt of the compound or prodrug according to claim 1, wherein G is a single bond.

6. A compound, a prodrug thereof or a pharmaceutically acceptable salt of the compound or prodrug according to claim 1, wherein each of A and G is a single bond.

7. A prodrug or pharmaceutically acceptable salt of a compound represented by the formula (1):

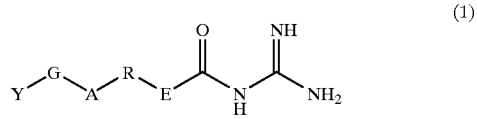

(1)

wherein E is a single bond; R is a substituted or unsubstituted indole; wherein the group represented by —C(O)NHC(NH)NH$_2$ in the formula (1) is attached to 2-position thereof;

A is a single bond or a substituted or unsubstituted lower alkylene group (one or more of the —CH$_2$— groups of said lower alkylene group may be replaced by one or more groups, which may be the same or different and are selected from the group consisting of a group represented by the formula: —O—, —S—, —N(R$^1$)— or —C(=O)—, a benzene ring and a cycloalkane ring (one or more of the —CH$_2$— groups in said cycloalkane ring may be replaced by one or more groups, which maybe the same or different and are represented by the formula: —O—, —S—, —N(R$^2$)— or —C(=O)—) and any two adjacent atoms of said lower alkylene group may form a double bond or a triple bond);

G is a single bond or a group represented by the formula: —O— or —N(R$^{11}$)—;

R$^1$, R$^{11}$ and R$^2$ are independently a hydrogen atom, a substituted or unsubstituted alkyl group, a substituted or unsubstituted alkenyl group, a substituted or unsubstituted alkynyl group, a substituted or unsubstituted cycloalkyl group, a substituted or unsubstituted cycloalkenyl group, a substituted or unsubstituted phenyl group, a substituted or unsubstituted naphthyl group, a substituted or unsubstituted heterocyclic group, or a substituted or unsubstituted acyl group; or a prodrug of said compound, or a pharmaceutically acceptable salt of said compound or prodrug;

Y is a group represented by the formula: —SO$_3$R$^{40}$, —P(=O)(OH)(OR$^{41}$), or —P(=O)(OR$^{42}$)(OR$^{43}$) wherein R$^{40}$, R$^{41}$, R$^{42}$, and R$^{43}$ are independently a substituted or unsubstituted alkyl group.

8. A compound, a prodrug thereof or a pharmaceutically acceptable salt of the compound or prodrug according to claim 1, which is selected from the group consisting of 2-[[[amino(imino)methyl]amino]carbonyl]-1-methyl-4-(trifluoromethyl)-1H-indol-6-yl hydrogen sulfate, 2-[[[amino(imino)methyl]amino]carbonyl]-1-methyl-4-

(trifluoromethyl)-1H-indol-7-yl hydrogen sulfate, [2-[[[amino(imino)methyl]amino]carbonyl]-1-methyl-4-(trifluoromethyl)-1H-indol-6-yl]methyl-phosphonic acid and 3-[2-[[[amino(imino)methyl]amino]-carbonyl]4-chloro-1H-indol-1-yl]-1-propanesulfonic acid.

9. A pharmaceutical composition comprising a compound, a prodrug thereof or a pharmaceutically acceptable salt of the compound or prodrug according to claim 1.

10. A method for treating hypertension, arrhythmia, angina pectoris, cardiac insufficiency, cardiac hypertrophy, diabetes mellitus, cardiac ischemic reperfusion-injury, acute renal failure, disorder induced by surgical treatment, atherosclerosis, pulmonary fibrosis, hepatic fibrosis, renal fibrosis, glomerular nephrosclerosis, organ hypertrophy, prostatic hypertrophy, diabetic complications or restenosis after PTCA, which comprises administering a compound, a prodrug thereof or a pharmaceutically acceptable salt of the compound or prodrug according to claim 1 to an object for the administration, in an effective amount.

* * * * *